US008809299B2

(12) United States Patent
Bhatia et al.

(10) Patent No.: US 8,809,299 B2
(45) Date of Patent: Aug. 19, 2014

(54) COMBINATION THERAPY FOR THE TREATMENT OF CANCER

(71) Applicants: Mickie Bhatia, Hamilton (CA); Eleftherios Sachlos, Hamilton (CA)

(72) Inventors: Mickie Bhatia, Hamilton (CA); Eleftherios Sachlos, Hamilton (CA)

(73) Assignee: McMaster University, Hamilton, ON (CA)

( * ) Notice: Subject to any disclaimer, the term of this patent is extended or adjusted under 35 U.S.C. 154(b) by 0 days.

(21) Appl. No.: 13/837,115

(22) Filed: Mar. 15, 2013

(65) Prior Publication Data

US 2013/0261074 A1 Oct. 3, 2013

Related U.S. Application Data

(60) Provisional application No. 61/616,658, filed on Mar. 28, 2012.

(51) Int. Cl.
*A01N 43/04* (2006.01)
*A61K 31/70* (2006.01)

(52) U.S. Cl.
USPC ............ 514/46; 514/42; 514/43; 514/45

(58) Field of Classification Search
None
See application file for complete search history.

(56) References Cited

U.S. PATENT DOCUMENTS

| | | | |
|---|---|---|---|
| 2004/0072824 | A1 | 4/2004 | Telerman et al. |
| 2011/0224141 | A1 | 9/2011 | Thompson et al. |

FOREIGN PATENT DOCUMENTS

| | | |
|---|---|---|
| WO | 2005/027842 | 3/2005 |
| WO | 2009148623 | 12/2009 |
| WO | 2013/143000 | 10/2013 |

OTHER PUBLICATIONS

Lowenberg, B., et al. "Cytarabine Dose for Acute Myeloid Leukemia." New England Journal of Medicine, Mar. 17, 2011, vol. 364, No. 11, pp. 1027-1036.
Gil-Ad, et al. "Phenothiazines induce apoptosis in a B16 mouse melanoma cell line and attenuate in vivo melanoma tumor growth." Oncology Reports, Jan. 2006, vol. 15, No. 1, pp. 107-112.
Chadwick, K., et al. "Cytokines and BMP-4 promote hematopoietic differentiation of human embryonic stem cells." Blood, 2006, 102, pp. 906-915.
Dalton, S.O., et al. "Cancer risk among users of neuroleptic medication: a population-based cohort study." Br J Cancer, 2006, 95, pp. 934-939.
Dalton, S.O., et al. "Risk for cancer in a cohort of patients hospitalized for schizophrenia in Denmark, 1969-1993." Schizophr Res., 2005, 75, pp. 315-324.
Desbordes, S.C., et al. "High-throughput screening assay for the identification of compounds regulating self-renewal and differentiation in human embryonic stem cells." Cell Stem Cell, 2008, 2, pp. 602-612.
Eppert, K., et al. "Stem cell gene expression programs influence clinical outcome in human leukemia." Nature Medicine doi:10.1038/nm.2415, 2011.
Estey, E., and Dohner, H. "Acute myeloid leukaemia." Lancet, 2006, 368, 1894-1907.
Estey, E.H., et al. "Randomized phase II study of fludarabine + cytosine arabinoside + idarubicin +/− all-trans retinoic acid +/− granulocyte colony-stimulating factor in poor prognosis newly diagnosed acute myeloid leukemia and myelodysplastic syndrome." Blood, 1999, 93, 2478-2484.
Grant, S. "New agents for AML and MDS." Best Practice & Research Clinical Haematology, 2009, 22, 501-507.
Gupta, P.B., et al. "Identification of selective inhibitors of cancer stem cells by high-throughput screening." Cell, 2009, 138, 645-659.
Parker, W.B., "Enzymology of Purine and Pyrimidine Antimetabolites Used in the Treatment of Cancer" Chem Rev., 2009, 109(7): 2880-2893.
Raj, L., et al. "Selective killing of cancer cells by a small molecule targeting the stress response to ROS." Nature, 2011, 475, 231-234.
Recher, C., et al. "Antileukemic activity of rapamycin in acute myeloid leukemia." Blood, 2005, vol. 105, No. 6, 2527-2534.
Sanz, M.A. "Treatment of acute promyelocytic leukemia." Hematology Am Soc Hematol Educ Program, 2006, 147-155.
Sanz, M.A., et al. "Management of acute promyelocytic leukemia: recommendations from an expert panel on behalf of the European Leukemia Net." Blood, 2009, 113, 1875-1891.
Tefferi, A., et al. "The 2008 World Health Organization Classification System for Myeloproliferative Neoplasms. Order Out of Choas." Cancer, Sep. 1, 2009, pp. 3842-3847.
Vannucchi, A.M., et al. "Advances in Understanding and Management of Myeloproliferative Neoplasms." CA Cancer J. Clin., 2009, 59(3):171-191.
Werbowetski-Ogilvie, T. E., et al. "Characterization of human embryonic stem cells with features of neoplastic progression." Nat Biotechnol., 2009, vol. 27, No. 1, 91-97.
Zhelev, Z., et al. "Phenothiazines suppress proliferation and induce apoptosis in cultured leukemic cells without any influence on the viability of normal lymphocytes. Phenothiazines and leukemia." Cancer Chemother Pharmacol., 2004, 53, 267-275.
Adewumi, O., et al. "Characterization of human embryonic stem cell lines by the International Stem Cell Initiative." Nat Biotechnol., 2007, 25, 803-816.
Beaulieu, J. M., and Gainetdinov, R. R. "The physiology, signaling, and pharmacology of dopamine receptors." Pharmacol Rev., 2011, 63, 182-217.

(Continued)

Primary Examiner — Patrick Lewis
(74) Attorney, Agent, or Firm — Bereskin & Parr LLP/S.E.N.C.R.L., s.r.l.; Micheline Gravelle

(57) ABSTRACT

Described are methods and compositions for treating cancer that include a dopamine receptor (DR) antagonist such as thioridazine and a chemotherapeutic agent. Optionally, the chemotherapeutic agent is a DNA synthesis inhibitor such as cytarabine or a microtubule inhibitor such as paclitaxel or docetaxel. The methods and compositions are useful for the treatment of cancers such as acute myeloid leukemia.

20 Claims, 31 Drawing Sheets

(56) References Cited

OTHER PUBLICATIONS

Ben-Porath, I., et al. "An embryonic stem cell-like gene expression signature in poorly differentiated aggressive human tumors." Nat Genet., 2008, 40, 499-507.
Bhatia, M., et al. "Purification of primitive human hematopoietic cells capable of repopulating immune-deficient mice." Proc Natl Acad Sci USA, 1997, 94, 5320-5325.
Bonnet, D., and Dick, J. E. "Human acute myeloid leukemia is organized as a hierarchy that originates from a primitive hematopoietic cell." Nat Med, 1997, 3, 730-737.
Boyer, L. A., et al. "Core transcriptional regulatory circuitry in human embryonic stem cells." Cell, 2005, 122, 947-956.
Breitman, T. R., et al. "Terminal differentiation of human promyelocytic leukemic cells in primary culture in response to retinoic acid." Blood, 1981, 57, 1000-1004.
Breitman, T. R., et al. "Induction of differentiation of the human promyelocytic leukemia cell line (HL-60) by retinoic acid." Proc Natl Acad Sci USA, 1980, 77, 2936-2940.
Burnett, A. K., et al. "The impact on outcome of the addition of all-trans retinoic acid to intensive chemotherapy in younger patients with nonacute promyelocytic acute myeloid leukemia: overall results and results in genotypic subgroups defined by mutations in NPM1, FLT3, and CEBPA." Blood, 2010, 115, 948-956.
Diallo, J. S., et al. "A high-throughput pharmacoviral approach identifies novel oncolytic virus sensitizers." Mol Ther. 2010, 18, 1123-1129.
Dick, J. E. "Stem cell concepts renew cancer research." Blood, 2008, 112, 4793-4807.
Dick, J. E. "Looking ahead in cancer stem cell research." Nat Biotechnol., 2009, 27, 44-46.
Driver, J. A., et al. "A prospective cohort study of cancer incidence following the diagnosis of Parkinson's disease." Cancer Epidemiol Biomarkers Prev., 2007, 16, 1260-1265.
Fibach, E., et al. "Control of normal differentiation of myeloid leukemic cells to macrophages and granulocytes." Proc Natl Acad Sci USA, 1973, 70, 343-346.
Frese, K. K., and Tuveson, D. A. "Maximizing mouse cancer models." Nat Rev Cancer, 2007, 7, 645-658.
Friend, C., et al. Hemoglobin synthesis in murine virus-induced leukemic cells in vitro: stimulation of erythroid differentiation by dimethyl sulfoxide. Proc Natl Acad Sci USA, 1971, 68, 378-382.
Grant, S. "New agents for AML and MDS." Best Practice & Research Clinical Haematology 22, 2009, 501-507.
Guan, Y. et al. "Detection, isolation, and stimulation of quiescent primitive leukemic progenitor cells from patients with acute myeloid leukemia (AML)." Blood, 2003, 101, 3142-3149.
Gupta, P. B., et al. "Identification of selective inhibitors of cancer stem cells by high-throughput screening." Cell, 2009, 138, 645-659.
Hotta, A., et al. "Isolation of human iPS cells using EOS lentiviral vectors to select for pluripotency." Nat Methods, 2009, 6, 370-376.
Inglese, J., et al. "Reporting data from high-throughput screening of small-molecule libraries." Nat Chem Biol., 2007, 3, 438-441.
Jemal, A., et al. "Cancer statistics." CA Cancer J Clin., 2010, 60, 277-300.
Jordan, C. T. "Cancer stem cells: controversial or just misunderstood?" Cell Stem Cell, 2009, 4, 203-205.
Koistinen, P. et al. "Regulation of the acute myeloid leukemia cell line OCI/AML-2 by endothelial nitric oxide synthase under the control of a vascular endothelial growth factor signaling system." Leukemia. Sep. 2001;15 (9):1433-41.
Lapidot, T., et al. "A cell initiating human acute myeloid leukaemia after transplantation into SCID mice." Nature, 1994, 367, 645-648.
Lee, J. Y., et al. "mTOR activation induces tumor suppressors that inhibit leukemogenesis and deplete hematopoietic stem cells after Pten deletion." Cell Stem Cell, 2010, 7, 593-605.
Li, X., et al. "Intrinsic resistance of tumorigenic breast cancer cells to chemotherapy." J Natl Cancer Inst., 2008, 100, 672-679.
Little, K. Y., et al. "Cocaine induction of dopamine transporter trafficking to the plasma membrane." Mol Pharmacol., 2002, 61, 436-445.
Nasr, R., et al. "Eradication of acute promyelocytic leukemia-initiating cells through PML-RARA degradation." Nat Med., 2008, 14, 1333-1342.
Nichols, J., et al. "Formation of pluripotent stem cells in the mammalian embryo depends on the POU transcription factor Oct4." Cell, 1998, 95, 379-391.
Niu, C., et al. "Studies on treatment of acute promyelocytic leukemia with arsenic trioxide: remission induction, follow-up, and molecular monitoring in 11 newly diagnosed and 47 relapsed acute promyelocytic leukemia patients." Blood, 1999, 94, 3315-3324.
Niwa, H., et al. "Quantitative expression of Oct-3/4 defines differentiation, dedifferentiation or self-renewal of ES cells." Nat Genet., 2000, 24, 372-376.
Regenthal, R., et al. "Drug levels: therapeutic and toxic serum/plasma concentrations of common drugs." J Clin Monit Comput., 1999, 15, 529-544.
Reya, T., et al. "Stem cells, cancer, and cancer stem cells." Nature, 2001, 414, 105-111.
Sachs, L. "Control of normal cell differentiation and the phenotypic reversion of malignancy in myeloid leukaemia." Nature, 1978, 274, 535-539.
Sachs, L. "The differentiation of myeloid leukaemia cells: new possibilities for therapy." Br J Haematol., 1978, 40, 509-517.
Shoemaker, R. H. "The NCI60 human tumour cell line anticancer drug screen." Nat Rev Cancer, 2006, 6, 813-823.
Sibley, D. R., and Monsma, F. J., Jr., "Molecular biology of dopamine receptors." Trends Pharmacol Sci., 1992, 13, 61-69.
Smith, B. D., et al. "Single-agent CEP-701, a novel FLT3 inhibitor, shows biologic and clinical activity in patients with relapsed or refractory acute myeloid leukemia." Blood, 2004, 103, 3669-3676.
Smith, T. J., et al. "2006 update of recommendations for the use of white blood cell growth factors: an evidence-based clinical practice guideline." J Clin Oncol., 2006, 24, 3187-3205.
Taussig, D. C., et al. "Anti-CD38 antibody-mediated clearance of human repopulating cells masks the heterogeneity of leukemia-initiating cells." Blood, 2008, 112, 568-575.
Visvader, J. E., and Lindeman, G. J. "Cancer stem cells in solid tumours: accumulating evidence and unresolved questions." Nat Rev Cancer, 2008, 8, 755-768.
Wang, Z. Y., and Chen, Z. "Acute promyelocytic leukemia: from highly fatal to highly curable." Blood, 2008, 111, 2505-2515.
Xu, R. H., et al. "BMP4 initiates human embryonic stem cell differentiation to trophoblast." Nat Biotechnol., 2002, 20, 1261-1264.
Yilmaz, O. H., et al. "Pten dependence distinguishes haematopoietic stem cells from leukaemia-initiating cells." Nature, 2006, 441, 475-482.
Ying, Q. L., et al. "BMP induction of Id proteins suppresses differentiation and sustains embryonic stem cell self-renewal in collaboration with STAT3." Cell, 2003, 115, 281-292.
Yoshida, H., et al. "Accelerated degradation of PML-retinoic acid receptor alpha (PML-RARA) oncoprotein by all-trans-retinoic acid in acute promyelocytic leukemia: possible role of the proteasome pathway." Cancer Res., 1996, 56, 2945-2948.
Zheng, R., et al. "Targeted inhibition of FLT3 overcomes the block to myeloid differentiation in 32Dcl3 cells caused by expression of FLT3/ITD mutations." Blood, 2002, 100, 4154-4161.
Zhu, J., et al. "Arsenic-induced PML targeting onto nuclear bodies: implications for the treatment of acute promyelocytic leukemia." Proc Natl Acad Sci USA, 1997, 94, 3978-3983.
International Search Report and Written Opinion dated May 21, 2013 for PCT Application No. PCT/CA2013/050255 (WO2013/143000).

A

B

Thio = Thioridazine 10uM
Chlor = Chlorpromazine 10uM

C

D

A

B

E

F

Each point, n=3; mean ± SD
(*) p<0.05, () p<0.01, (*) p<0.001, (****) p<0.0001.

COMBINATION THERAPY FOR THE TREATMENT OF CANCER

RELATED APPLICATIONS

This application claims priority to U.S. Provisional Patent Application No. 61/616,658 filed Mar. 28, 2012, the contents of which are incorporated by reference herein in their entirety.

FIELD OF THE DISCLOSURE

The disclosure relates to methods and compositions for the treatment of cancer and particularly to methods and compositions for the treatment of cancer with a dopamine receptor antagonist and chemotherapeutic agent.

BACKGROUND OF THE DISCLOSURE

Increasing evidence suggests that cancer/tumor development is due to a rare population of cells, termed cancer stem cells (CSCs) (Dick, 2009; Jordan, 2009; Reya et al., 2001) that are uniquely able to initiate and sustain disease. In addition, experimental evidence indicates that conventional chemotherapeutics, characterized by their ability to inhibit cell proliferation of cancer cell lines (Shoemaker, 2006) or reduce tumor burden in murine models (Frese and Tuveson, 2007), are ineffective against human CSCs (Guan et al., 2003; Li et al., 2008). This resistance to chemotherapeutics is coupled with indiscriminate cytotoxicity that often affects healthy stem and progenitor cells, leading to dose restriction and necessitating supportive treatment (Smith et al., 2006). Recent examples along these lines include selective induction of apoptosis (Gupta et al., 2009; Raj et al., 2011) that remains to be tested in normal SCs and in the human system. Accordingly, the identification of agents that target CSCs alone is now critical to provide truly selective anti-cancer drugs for pre-clinical testing.

Normal and neoplastic SCs are functionally defined by a tightly controlled equilibrium between self-renewal vs. differentiation potential. In the case of CSCs, this equilibrium shifts towards enhanced self-renewal and survival leading to limited differentiation capacity that eventually allows for tumor growth. In contrast to direct toxic effects that equally affect normal SCs, an alternative approach to eradicate CSCs is by modification of this equilibrium in favor of differentiation in an effort to exhaust the CSC population. The identification of molecules that selectively target somatic CSCs while sparing healthy SC capacity would therefore be useful for the development of novel diagnostics and therapeutic treatments to selectively target human CSCs.

Hematological malignancies are types of cancer that affect blood, bone marrow and lymph nodes. Hematological malignancies may derive from either of the two major blood cell lineages: myeloid and lymphoid cell lines. Examples of myeloid malignancies include acute myeloid leukemia and chronic myeloid leukemia.

While myeloid malignancies are all generally considered to arise from precursors of the myeloid lineage in the bone marrow, they are highly divergent in presentation, pathology and treatment. For example, the 2008 World Health Organization Classification for Myeloproliferative Neoplasms (See Tefferi et al. *Cancer*, September 1$^{st}$, pp. 3842-3847 (2009); also Vannucchi et al. Advances in Understanding and Management of Myeloproliferative Neoplasms *CA Cancer J. Clin.* 2009; 59:171-191, both hereby incorporated by reference), identifies 5 different classification schemes for myeloid neoplasms, and places acute myeloid leukemia (AML) in a separate category from chronic myelogenous leukemia (CML) and other myeloproliferative neoplasms. Furthermore, CML is often characterized as containing the BCR-Abl translocation which is absent in AML. Preferred treatments for leukemias, such as myeloid malignancies, would target leukemic cells without unduly affecting hematopoietic stem cell populations.

Thioridazine is a dopamine receptor antagonist that belongs to the phenothiazine drug group and is used as an anti-psychotic. It has been in clinical use since 1959, however because of concerns about cardiotoxicity and retinopathy at high doses this drug is not commonly prescribed, and is reserved for patients who have failed to respond to, or have contraindications for more widely used antipsychotics. Schizophrenic patients receiving dopamine receptor antagonist medication at doses deemed effective for schizophrenia have been reported to have a reduced incidence of rectum, colon, and prostate cancer compared to the general population.

Cytarabine (AraC) is a DNA synthesis inhibitor and the gold-standard chemotherapeutic used in both induction and consolidation therapy of adult human AML. However, this treatment poses significant morbidity and mortality risks at high doses (Estey and Dohner, 2006).

There is a need for novel methods and compositions for the treatment of cancer and in particular for methods for the treatment and prognosis of acute myeloid leukemia.

SUMMARY OF THE DISCLOSURE

It has been determined that the combination of a dopamine receptor (DR) antagonist and a chemotherapeutic agent such as a DNA synthesis inhibitor is surprisingly effective for killing cancer cells. As shown herein, dopamine receptor antagonists such as thioridazine, chlorpromazine, fluphenazine or prochlorperazine are cytotoxic to cancer cells and in particular acute myeloid leukemia (AML). Dopamine receptors antagonists at concentrations toxic to cancer cells have also been found to have a relatively limited effect on normal stem cells such as hematopoietic stem cells. Furthermore, as shown in Examples 13 and 15, the combination of the DR antagonist thioridazine and the chemotherapeutic agent cytarabine resulted in a synergistic effect and a significant reduction in the number of AML cancer cells. The combination of thioridazine and cytarabine was also shown to eliminate AML cancer cells while preserving normal hematopoietic stem cell function. The use of a DR antagonist in combination with a chemotherapeutic agent such as cytarabine therefore allows for a therapeutically effective dose of chemotherapeutic agents to be administered at lower levels, thereby avoiding the undesirable sides effects usually associated with higher doses of chemotherapeutic agents.

Accordingly, one aspect of the disclosure includes methods for treating cancer or a pre-cancerous disorder in a subject comprising administering to the subject a dopamine receptor (DR) antagonist and a chemotherapeutic agent. In one embodiment, the chemotherapeutic agent is a DNA synthesis inhibitor, such as cytarabine. In one embodiment, the chemotherapeutic agent is a microtubule inhibitor, such as a taxane. In one embodiment, the DR antagonist is a phenothiazine derivative such as thioridazine or a DR antagonist selected from Table 1. In one embodiment, the DR antagonist is an antibody selective for one or more dopamine receptors. In one embodiment, the cancer or pre-cancerous disorder is leukemia or lymphoma, optionally acute myeloid leukemia (AML).

Another aspect of the disclosure includes a method for inducing cell death in a cancer cell comprising contacting the cell with a dopamine receptor antagonist and a chemotherapeutic agent. A similar aspect of the disclosure includes a method for reducing the proliferation of a cancer cell comprising contacting the cell with a dopamine receptor antagonist and a chemotherapeutic agent. In one embodiment, the chemotherapeutic agent is a DNA synthesis inhibitor such as cytarabine. In one embodiment, the DR antagonist is a phenothiazine derivative such as thioridazine, or a compound selected from Table 1. In one embodiment, the DR antagonist is an antibody selective for one or more dopamine receptors. In one embodiment, the chemotherapeutic agent is a microtubule inhibitor, such as a taxane. In one embodiment, the cancer cell is a leukemic cell, optionally an AML cell. In one embodiment, the cancer cell is a cancer stem cell, optionally a leukemic cancer stem cell.

A further aspect of the disclosure includes a composition comprising a dopamine receptor antagonist and a chemotherapeutic agent. In one embodiment, the DR antagonist is a phenothiazine derivative such as thioridazine, or a compound selected from Table 1. In one embodiment, the chemotherapeutic agent is a DNA synthesis inhibitor such as cytarabine. Also provided is the use of a composition comprising a dopamine receptor antagonist and a chemotherapeutic agent as described herein for the treatment of cancer. Optionally, the composition comprises a DR antagonist conjugated to a chemotherapeutic agent. For example, in one embodiment there is provided a compound comprising a DR antagonist conjugated to a DNA synthesis inhibitor, such as cytarabine. In one embodiment, there is provided a DR antagonist conjugated to a microtubule inhibitor, such as taxol. In one embodiment, the DR antagonist is a phenothiazine derivative such as thioridazine or a compound selected from Table 1. In one embodiment, the DR antagonist is an antibody selective for one or more dopamine receptors.

In one aspect of the disclosure, there is provided a method for treating cancer or a pre-cancerous disorder in a subject comprising administering to the subject a dopamine receptor (DR) antagonist and a radiation therapy. Optionally, the method also includes administering to the subject a chemotherapeutic agent as described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

One or more embodiments of the disclosure will now be described in relation to the drawings in which.

DETAILED DESCRIPTION

I. Definitions

Figure 1:
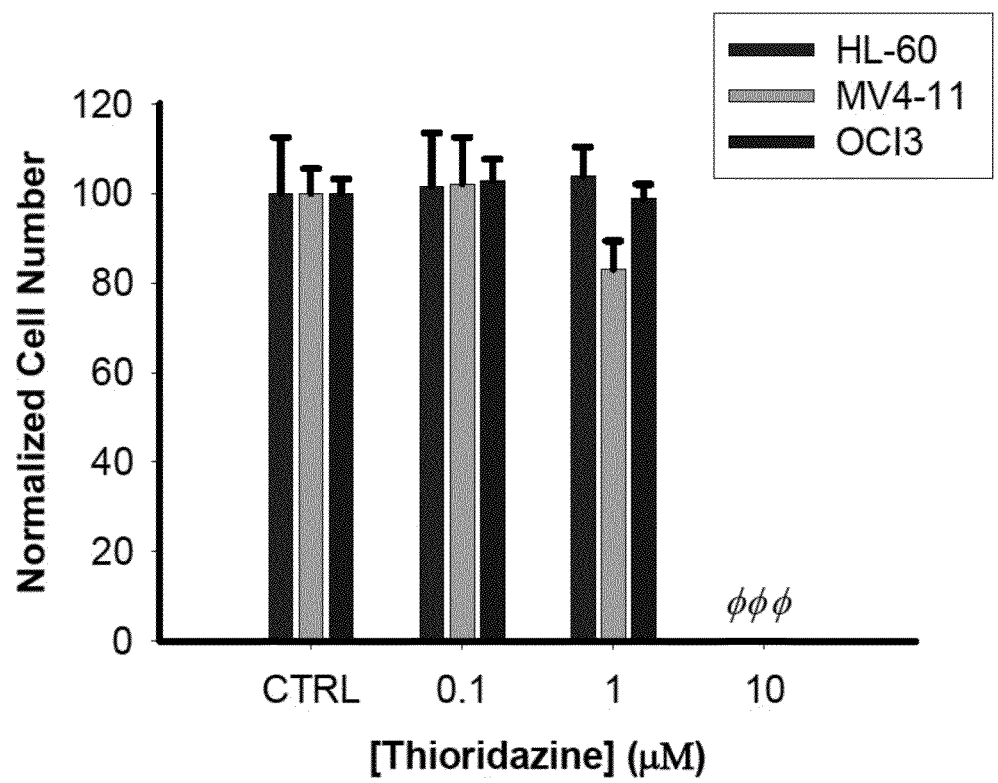
FIG. 1 shows thioridazine at 10 µM is cytotoxic to leukemic cell lines HL-60, MV4-11 and OCI3.

As used herein, the term "cancer" refers to one of a group of diseases caused by the uncontrolled, abnormal growth of cells that can spread to adjoining tissues or other parts of the body. Cancer cells can form a solid tumor, in which the cancer cells are massed together, or exist as dispersed cells, as in leukemia.

The term "cancer cell" as used herein refers a cell characterized by uncontrolled, abnormal growth and the ability to invade another tissue or a cell derived from such a cell. Cancer cell includes, for example, a primary cancer cell obtained from a patient with cancer or cell line derived from such a cell. Similarly, a "hematological cancer cell" refers to a cancer cell deriving from a blood cell or bone marrow cell. Examples of cancer cells include, but are not limited to, cancer stem cells, breast cancer cells, rectum cancer cells, colon cancer cells, prostate cancer cells and hematological cancer cells such as myelomas, leukemic cells or lymphoma cells.

As used herein the term "cancer stem cell" refers to a cell that is capable of self-renewal and differentiating into the lineages of cancer cells that comprise a tumor or hematological malignancy. Cancer stem cells are uniquely able to initiate and sustain the disease.

The term "precancerous disorder" as used herein refers to one of a group of hyperproliferative disorders that can develop into cancer, including for example precancerous blood disorders, such as myeloproliferative disease or myelodysplastic syndrome which is a premalignant condition that is related to and/or can develop into acute myeloid leukemia (AML).

The term "precancerous cell" as used herein refers to a cell characterized by uncontrolled, abnormal growth or a cell derived from such a cell. The term "precancerous cell" includes, for example, a primary precancerous cell obtained from a patient with precancerous disorder or cell line derived from such a cell or a cancer stem cell. Similarly, a "hematological precancerous cell" refers to a precancerous cell deriving from a blood cell or bone marrow cell. In one embodiment, the hematological precancerous cell is a myeloproliferative cell.

The term "leukemia" as used herein refers to any disease involving the progressive proliferation of abnormal leukocytes found in hemopoietic tissues, other organs and usually in the blood in increased numbers. "Leukemic cells" refers to leukocytes characterized by an increased abnormal proliferation of cells. Leukemic cells may be obtained from a subject diagnosed with leukemia.

The term "acute myeloid leukemia" or "acute myelogenous leukemia" ("AML") refers to a cancer of the myeloid line of blood cells, characterized by the rapid growth of abnormal white blood cells that accumulate in the bone marrow and interfere with the production of normal blood cells. Pre-leukemic conditions such as myelodysplastic or myeloproliferative syndromes may also develop into AML.

As used herein, the term "monocytic leukemia" refers to a subtype of leukemia characterized by the expression of CD14, and includes Acute Monocytic Leukemia, which is a subtype of acute myeloid leukemia. In one embodiment, a subject is identified as having acute monocytic leukemia if they have greater than 20% blasts in the bone marrow, and of these, greater than 80% are of the monocytic lineage.

The term "dopamine receptor antagonist" refers to a compound that produces any detectable or measurable reduction in the function or activity of one or more dopamine receptors. For example, in one embodiment the dopamine receptor antagonist is an antibody selective for one or more dopamine receptors. In one embodiment, the dopamine receptors (DR) are selected from DR1, DR2, DR3, DR4 and DR5. Dopamine receptor antagonists may be selective for one or multiple dopamine receptors, i.e. a "multi-receptor antagonist". Examples of multi-receptor dopamine antagonists include thioridazine and chlorpromazine. Dopamine receptors are commonly grouped in $D_1$-family dopamine receptors (DR1 and DR5) and $D_2$-family dopamine receptors (DR2, DR3 and DR4). In one embodiment, the dopamine receptor antagonist is a compound selected from those listed in Table 1.

TABLE 1

Dopamine antagonists suitable for use in the methods described herein.

| Dopamine Receptor Antagonist | Mechanism of Action |
|---|---|
| Acetopromazine maleate salt | Dopaminergic antagonist |
| Amisulpride | D2 and D3 receptor antagonist |
| Amoxapine | Dopamine-reuptake inhibitor |
| Azaperone | Dopaminergic receptor antagonist |
| Benperidol | Dopamine antagonist |
| Benzo[a]phenanthridine-10,11-diol, 5,6,6a,7,8,12b-hexahydro-, trans- [CAS] | D1 ligand |
| Bromopride | Dopamine antagonist |
| Bromperidol | Dopamine antagonist |

TABLE 1-continued

Dopamine antagonists suitable for use in the methods described herein.

| Dopamine Receptor Antagonist | Mechanism of Action |
|---|---|
| Chlorpromazine hydrochloride | D2 antagonist, selective D1, D3, D4 & D5 |
| Chlorprothixene hydrochloride | D2 dopamine receptor antagonist |
| Clomipramine hydrochloride | chlorpromazine derivative |
| Disulfiram | Dopamine beta-hydroxylase inhibitor |
| DO 897/99 | D3 antagonist |
| Domperidone | Dopamine Antagonists |
| DROPERIDOL | D2 (dopamine receptor) antagonist |
| Ethopropazine hydrochloride | Thioridazine derivative |
| Fluperlapine | D2 (dopamine receptor) antagonist |
| Fluphenazine dihydrochloride | Dopamine antagonist D1 & D2 antagonist |
| GBR 12909 dihydrochloride | Dopamine reuptake inhibitor |
| Haloperidol | Dopamine antagonist D2, non-selective antagonist |
| Hydrastinine hydrochloride | Dopamine receptor blocker |
| Indatraline | potent D antagonist |
| Itopride | Dopamine D2 receptors and ACE inhibition |
| LEVOSULPIRIDE | D2, D3, & D4 antagonist |
| Loxapine succinate | Dopamine antagonist/D2, D4 |
| Mesoridazine | D2 antagonist |
| Mesoridazine besylate | D antagonist |
| Methotrimeprazine maleat salt | Thioridazine derivative |
| Metixene hydrochloride | Thioridazine derivative |
| Molindone hydrochloride | Dopamine receptor antagonist |
| Nafadotride | D3 antagonist |
| Nomifensine maleate | Dopamine uptake inhibitor |
| OLANZAPINE | D1 & D2 antagonist |
| PEROSPIRONE HCl | D2 & D4 antagonist |
| Perphenazine | D1 & D2 antagonist |
| PHENOTHIAZINE | Thioridazine derivative |
| Pimozide | Dopamine antagonist |
| Piperacetazine | Thioridazine derivative |
| Prochlorperazine | Thioridazine derivative |
| Prochlorperazine dimaleate | Dopamine antagonist |
| Promazine hydrochloride | Dopamine receptor antagonist |
| Promethazine hydrochloride | Thioridazine derivative |
| Quetiapine | dopamine and serotonin receptors antagonist |
| QUETIAPINE HEMIFUMARATE | D2 antagonist |
| R(+)-SCH-23390 hydrochloride | D1 antagonist |
| Raclopride | D2 antagonist |
| Remoxipride Hydrochloride | Dopaminergic antagonist |
| RISPERIDONE | D1 & D2 antagonist |
| S(−)Eticlopride hydrochloride | Dopamine receptor antagonist |
| Sertindole | Dopamine D2/Serotonin 5-HT2 receptor antagonist |
| SKF 83566 | D1 antagonist |
| Spiperone | D2 antagonist |
| Sulpiride | D2 antagonist |
| Sulpiride | D2 & D3 antagonist |
| Thiethylperazine malate | Thioridazine derivative |
| Thioproperazine dimesylate | D1 & D2 antagonist |
| Thioridazine hydrochloride | Thioridazine derivative |
| Trifluoperazine Dihydrochloride | D2 antagonist |
| Triflupromazine hydrochloride | D1 & D2 antagonist |
| Trimeprazine tartrate | Thioridazine derivative |
| Trimethobenzamide hydrochloride | D2 antagonist |
| Ziprasidone Hydrochloride | Dopamine D2/serotonin 5-HT2 antagonist |
| Zotepine | Dopamine D2/serotonin 5-HT2 antagonist |

As used herein, the term "phenothiazine" or "phenothiazine derivative" refers to a compound that is derived from or contains a phenothiazine moiety or backbone. Phenothiazine has the formula $S(C_6H_4)_2NH$ and phenothiazine derivatives comprise one or more substitutions or additions to phenothiazine. For example, some phenothiazine derivatives have a three-ring structure in which two benzene rings are linked by a nitrogen and a sulfur. Examples of phenothiazine derivatives include, but are not limited to, thioridazine, chlorpromazine, levomepromazine, mesoridazine, fluphenazine, perphenazine, prochlorperazine, and trifluoperazine. Additional examples of phenothiazine derivatives for use in the methods of the present disclosure are set out in Table 1. In one embodiment, thioridazine has the IUPAC name 10-{2-[(RS)-1-Methylpiperidin-2-yl]ethyl}-2-methylsulfanylphenothiazine. Optionally, one or more racemic forms of a phenothiazine derivative such as thioridazine are used in the methods described herein.

As used herein, the term "chemotherapeutic agent" refers to a chemical or chemicals useful for the treatment of cancer. Examples of chemotherapeutic agents include anti-proliferative or antineoplastic agents that inhibit cell division and/or DNA synthesis. Further examples of chemotherapeutic agents suitable for use in the methods and compositions described herein include those listed in Steven Grant, "New agents for AML and MDS" *Best Practice & Research Clinical Haematology* 22 (2009) 501-507. Still further examples of chemotherapeutic agents suitable for use in the methods and compositions described herein include those listed on http://www.cancer.org/Treatment/TreatmentsandSideEffects/TreatmentTypes/Chemotherapy/ChemotherapyPrinciplesAnIn-depthDiscussionoftheTechniquesanditsRoleinTreatment/chemotherapy-principles-types-of-chemo-drugs. Other examples of chemotherapeutic agents suitable for use in the methods and compositions described herein include agents suitable for the treatment of AML such as mitoxantrone (a DNA topioisomerase inhibitor) and daunorubicin (a DNA intercalator).

As used herein the term "DNA synthesis inhibitor" refers to a chemotherapeutic agent that inhibits or prevents the synthesis of DNA by a cancer cell. Examples of DNA synthesis inhibitors include, but are not limited to, cytarabine, 6-mercaptopurine, 6-thioguanine, 5-fluorouracil, capecitabine, floxuridine, gemcitabine, decitabine, vidaza, fludarabine, nelarabine, cladribine, clofarabine, pentostatin, thiarabine, troxacitabine, sapacitabine or forodesine as well as purine and pyrimidine antimetabolites as described in William B. Parker "Enzymology of Purine and Pyrimidine Antimetabolites Used in the Treatment of Cancer" *Chem Rev.* 2009 July; 109(7): 2880-2893. In one embodiment, the DNA synthesis inhibitor is cytarabine or another deoxycytidine analogue as described herein. In one embodiment, the DNA synthesis inhibitor is a DNA elongation terminator and functions in a similar way to cytarabine such as fludarabine, nelarabine, cladribine, or clofarabine.

As used herein, "cytarabine" refers to a compound comprising a cytosine base and a arabinose sugar that is converted into Arabinofuranosylcytosine triphosphate in vivo. Cytarabine is also known as known as cytosine arabinoside or Ara-C (Arabinofuranosyl Cytidine).

As used herein, a "microtubule inhibitor" refers to a chemotherapeutic agent that interferes with the normal function or processing of microtubules during mitosis. Examples of microtubule inhibitors include, but are not limited to, taxanes such as paclitaxel or docetaxel and vinca alkaloids such as vinblastine, vincristine, vindesine, and vinorelbine.

As used herein, "reducing the proliferation of a cancer cell" refers to a reduction in the number of cells that arise from a cancer cell as a result of cell growth or cell division and includes cell death or differentiation of a cancer stem cell. The term "cell death" as used herein includes all forms of cell death including necrosis and apoptosis. As used herein "differentiation of a cancer stem cell" refers to the process by which a cancer stem cell loses the capacity to self-renew and cause the lineages of cancer cells that comprise a tumor or hematological malignancy.

Figure 17:
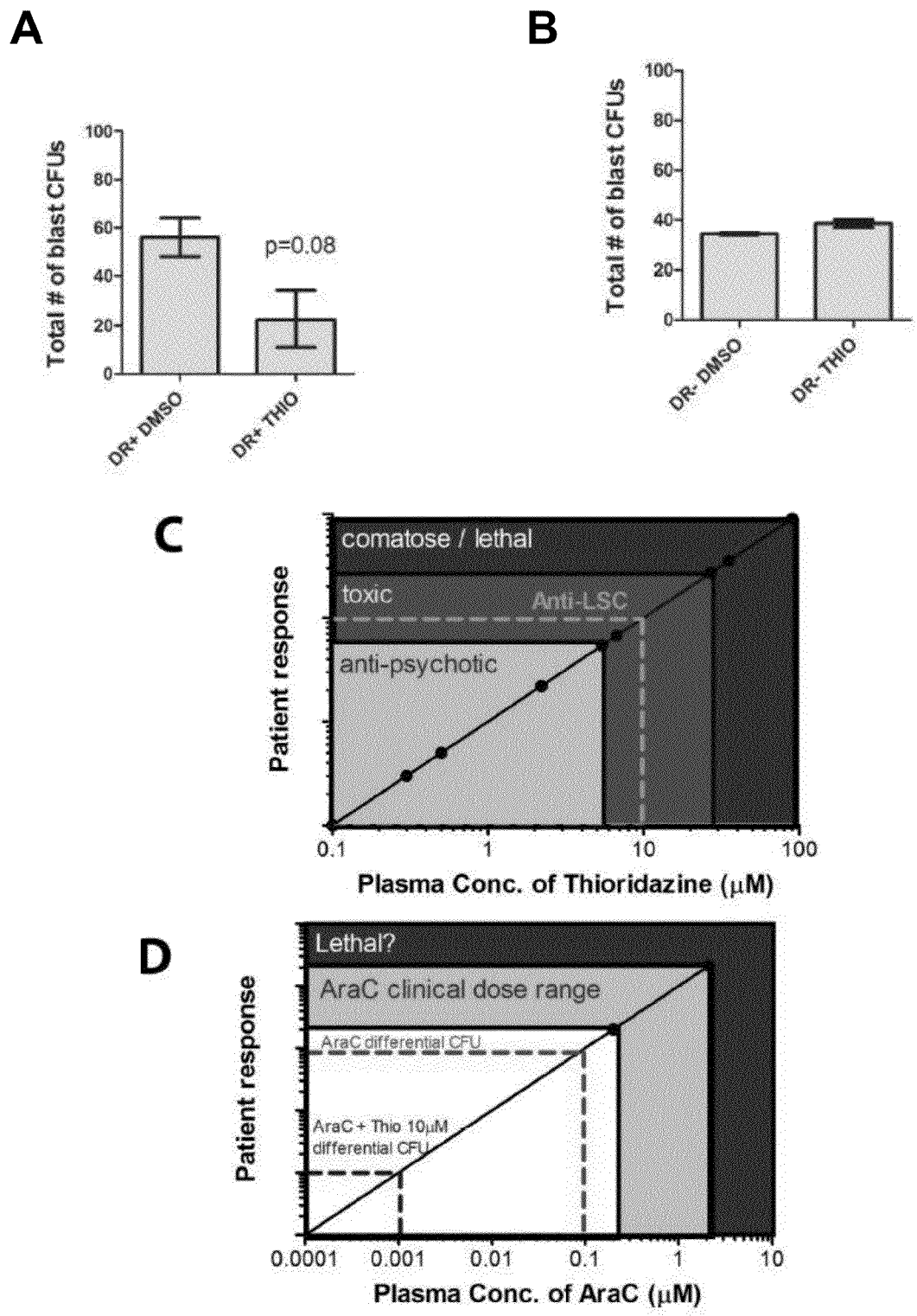
FIG. 17 shows the clinical utility of thioridazine and combination therapy with a DNA synthesis inhibitor. (A-B) Blast-CFU generation of fluorescence-activated cell sorted patient AML cells into (A) DR+ and (B) DR− subfractions treated with DMSO vehicle or thioridazine 10 μM (THIO). (C) Schematic showing the clinical range in which thioridazine is administered to schizophrenia patients. The concentration of thioridazine shown to induce an anti-LSC effect is plotted along with the patient response. (D) Schematic showing the clinical range in which AraC is administered to AML patients. The differential dose of AraC as a single treatment (AraC differential CFU) is plotted alongside the 100-fold reduction in AraC concentration when combined with thioridazine (AraC+Thio 10 µM differential CFU) in order to achieve the same targeted response to AML. Human plasma levels adapted from published data (Regenthal et al., 1999).

As used herein, the phrase "effective amount" or "therapeutically effective amount" means an amount effective, at dosages and for periods of time necessary to achieve the desired result. For example in the context or treating a cancer such as AML, an effective amount is an amount that for example induces remission, reduces tumor burden, and/or prevents tumor spread or growth of leukemic cells compared to the response obtained without administration of the compound. Effective amounts may vary according to factors such as the disease state, age, sex and weight of the animal. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. For example, FIGS. 17c and 17d show typical dosages and patient responses for thirodazine and AraC respectively.

As used herein "plasma concentration" refers to the total plasma concentration of a particular compound. For example, in one embodiment a plasma concentration of thioridazine of about 10 μM refers to the total plasma concentration of thioridazine including bound and unbound forms.

The term "pharmaceutically acceptable" means compatible with the treatment of animals, in particular, humans.

The term "subject" as used herein includes all members of the animal kingdom including mammals, and suitably refers to humans. Optionally, the term "subject" includes mammals that have been diagnosed with cancer or are in remission.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease (e.g. maintaining a patient in remission), preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. In one embodiment, treatment methods comprise administering to a subject a therapeutically effective amount of a dopamine receptor antagonist as described herein and optionally consists of a single administration, or alternatively comprises a series of administrations.

II. Methods and Uses

It has been found that dopamine receptor (DR) antagonists in combination with another chemotherapeutic agent are surprisingly effective in reducing the proliferation of cancer cells and/or inducing dell death in cancer cells. As shown in Example 13, the use of the DR antagonist thioridazine in combination with the DNA synthesis inhibitor cytarabine resulted in a significant reduction of the effective concentration of cytarabine required to reduce AML-blast-FCU while retaining hematopoietic pluripotent stem cell (HSPC) function. Furthermore, as shown in Example 15 and FIG. 19 the use of thioridazine in combination with cytarabine significantly reduced the viability of leukemic cells from AML patient derived cell lines.

Accordingly, in one embodiment there is provided a method of treating cancer or precancerous disorder in a subject comprising administering to the subject in need thereof a dopamine receptor antagonist and a chemotherapeutic agent. Also provided is a use of a dopamine receptor antagonist and a chemotherapeutic agent for the treatment of cancer or a precancerous disorder. In one embodiment the chemotherapeutic agent is a DNA synthesis inhibitor such as cytarabine. In one embodiment, the methods or uses described herein are useful to treat a precancerous disorder, such as a myeloproliferative disease. In one embodiment, the cancer is a leukemia such as acute myeloid leukemia (AML), or monocytic leukemia. The methods and uses described herein are particularly useful for the treatment of cancer cells that express dopamine receptors. In one embodiment, the methods and uses described herein are useful for the treatment of cancer cells that express the monocytic marker CD14. In one embodiment, the dopamine receptor antagonist preferentially induces the differentiation of cancer stem cells in the subject relative to hematopoietic or normal stem cells. In one embodiment, the cancer stem cells are leukemic cancer stem cells. In one embodiment, the subject has AML and the cancer stem cells are AML cancer stem cells.

In one embodiment, a therapeutically effective dose of a DR antagonist and a chemotherapeutic agent are administered to the subject. In one embodiment, the DR antagonist and the chemotherapeutic agent are administered to the subject at the same time, optionally as a composition comprising the DR antagonist and the chemotherapeutic agent, or as two separate doses. For example, in one embodiment, the DR antagonist and chemotherapeutic agent are conjugated together, either with or without a linker. In one embodiment, the DR antagonist and the chemotherapeutic agent are administered to the subject at different times. For example, in one embodiment, the DR antagonist is administered prior to, or after the chemotherapeutic agent. In one embodiment, the DR antagonist is administered prior to, or after the chemotherapeutic agent separated by a time of at least 1 minute, 2 minutes, 5 minutes, 10 minutes, 30 minutes, 45 minutes, 1 hour, 1.5 hours, 2 hours, 3 hours, 4 hours, 5 hours, 6 hours, 8 hours, 10 hours, 12 hours 16 hours, or 24 hours. Optionally, in some embodiments the DR antagonist and chemotherapeutic agent are administered to the subject separated by more than 24 hours, 36 hours, 48 hours, 3 days, 4 days, 5 days, 6 days, or one week.

In one embodiment, the dopamine receptor antagonists are antagonists for one or more of dopamine receptors (DR) such as DR1, DR2, DR3, DR4, and DR5. Optionally the DR antagonist is a multi-receptor antagonist, or is specific for a single dopamine receptor subtype. In one embodiment, the DR antagonist is a phenothiazine derivative such as thioridazine, chlorpromazine, fluphenazine, or prochlorperazine. In one embodiment, the DR antagonist is selected from the compounds listed in Table 1. In one embodiment, the DR antagonist is an antibody selective for one or more dopamine receptors. A person of skill in the art would readily be able to identify additional dopamine receptor antagonists that are useful for the treatment of cancer as described herein.

In one embodiment, the methods or uses described herein involve a phenothiazine derivative such as thioridazine, chlorpromazine, fluphenazine, or prochlorperazine. A person skilled in the art would readily be able to identify additional phenothiazine derivatives that are dopamine receptor antagonists and useful for the treatment of cancer as described herein. In one embodiment, the phenothiazine derivatives have a differential toxicity for cancer cells, such as leukemic cells, compared to normal stem cells or hematopoietic stem cells.

In one embodiment the methods or uses described herein involve a chemotherapeutic agent such as a DNA synthesis inhibitor. For example, in one embodiment the DNA synthesis inhibitor is cytarabine. In one embodiment, the DNA synthesis inhibitor has a similar structure or function to cytarabine. For example, in one embodiment the DNA synthesis inhibitor is a deoxycytidine analogue, such as gemcitabine, decitabine, vidaza, troxacitabine, thiarabine or sapacitabine. In one embodiment, the DNA synthesis inhibitor is a compound known to be useful for the treatment of AML such as cytarabine, 6-thioguanine, fludarabine, cladribine or clofarabine. In one embodiment, the DNA synthesis inhibitor is selected from cytarabine, 6-mercaptopurine, 6-thioguanine, 5-fluorouracil, capecitabine, floxuridine, gemcitabine, decitabine, vidaza, fludarabine, nelarabine, cladribine, clofarabine, pentostatin, thiarabine, troxacitabine, sapacitabine and forodesine. In one embodiment, the chemotherapeutic agent is an agent suitable for the treatment of AML such as mitoxantrone (a DNA topioisomerase inhibitor) or daunorubicin (a DNA intercalator).

In one embodiment, the DR antagonists and/or chemotherapeutic agents are prepared for administration to a subject in need thereof as known in the art. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

In one embodiment, the methods described herein provide specific levels of DR antagonists and chemotherapeutic agents suitable for administration to a subject in need thereof for the treatment of cancer. For example, in one embodiment, the combination of DR antagonist and a chemotherapeutic agent allows a smaller dose of the chemotherapeutic agent to be administered to the subject relative to what would be required if the chemotherapeutic agent was administered by itself in order to achieve a beneficial or desired result (see e.g. FIG. 17d). In one embodiment, the chemotherapeutic agent is cytarabine and the dose of cytarabine which would be administered to the subject results in a plasma concentration of cytarabine between 0.1 nM and 100 nM, optionally between 1 nM and 100 nM. In one embodiment, the dose of cytarabine which would be administered to the subject results in a plasma concentration of less than 5 nM, between 0.1 nM and 5 nM or between 0.5 and 2.5 nM. In one embodiment, the dose of cytarabine which would be administered to the subject results in a plasma concentration of between 0.0001 µM and 2 µM, or optionally between 0.001 µM and 2 µM. In one embodiment the dopamine receptor antagonist is thioridazine and the dose of thioridazine which would be administered to the subject results in a plasma concentration of thioridazine between 0.1 µM and 20 µM. In one embodiment, the dose of thioridazine which would be administered to the subject results in a plasma concentration of between 5 µM and 15 µM. In one embodiment, the dose of thioridazine which would be administered to the subject results in a plasma concentration of about 10 µM.

In one embodiment, cytarabine is administered to the subject such that the plasma concentration of cytarabine in the subject is between 1 nM and 100 nM and thioridazine is administered to the subject such that the plasma concentration of thioridazine in the subject is between 5 µM and 15 µM and optionally about 10 µM.

In one embodiment, there is also provided a method for reducing the proliferation or inducing cell death in a cancer cell or cells comprising contacting the cell with a dopamine receptor antagonist and a chemotherapeutic agent. In a similar embodiment there is provided a use of a dopamine receptor antagonist and a chemotherapeutic agent for reducing the proliferation of a cancer cell or cells. In one embodiment, the chemotherapeutic agent is a DNA synthesis inhibitor, such as cytarabine. In one embodiment, the DR antagonist is an antibody selective for one or more dopamine receptors. In one embodiment, the DR antagonist is a phenothiazine derivative such as thioridazine. In one embodiment, the DR antagonist induces differentiation or cell death of a cancer stem cell. In one embodiment, the DR antagonist induces cell death of a cancer cell. Optionally, the cancer cell may be in vivo or in vitro. The cancer cell may be a precancerous cell such as a myelodyplastic or myeloproliferative cell. In one embodiment, the cancer cell is a hematological cancer cell. In one embodiment, the cancer cell is a leukemic cell, such as a cell from a subject with AML. In one embodiment, the DR receptor antagonist is a phenothiazine derivative such as thioridazine, chlorpromazine, fluphenazine, or prochlorperazine. In one embodiment, the DR antagonist is selected from the compounds listed in Table 1. In one embodiment, the chemotherapeutic agent is a microtubule inhibitor, such as paclitaxel or docetaxel. Optionally, the chemotherapeutic agent and the DR antagonist are conjugated, either with or without a linker.

In one aspect of the disclosure, there is provided a method for reducing the proliferation of one or more cancer cells such as one or more leukemic cells. In one embodiment, the method comprises contacting the one or more cells with thioridazine and cytarabine. In one embodiment the leukemic cells are acute myeloid leukemia (AML) cells. Optionally, the leukemic cells are leukemic cancer stem cells. In one embodiment, the cells are in vivo or in vitro. In one embodiment, the cells are contacted with cytarabine at a concentration of about 0.1 to 100 nM, optionally about 1 nM to 100 nM. In one embodiment, the cells are contacted with cytarabine at a concentration of less than 5 nM, between 0.1 nM and 5 nM or between 0.5 and 2.5 nM. In one embodiment, cells are contacted with cytarabine at a concentration of between 0.0001 µM and 2 µM, or optionally between 0.001 µM and 2 µM. In one embodiment, the cells are contacted with thioridazine at a concentration between 0.1 µM and 20 µM. In one embodiment, the cells are contacted with thioridazine at a concentration between 5 µM and 15 µM. In one embodiment, the cells are contacted with thioridazine at a concentration of about 10 µM. In one embodiment, the cells are contacted with cytarabine at a concentration between 1 nM and 100 nM and the cells are contacted with thioridazine at a concentration between 5 µM and 15 µM, optionally about 10 µM.

In an aspect of the disclosure, there is provided a composition comprising a DR antagonist and a chemotherapeutic agent. Optionally, the DR antagonist and chemotherapeutic agent may be unconjugated or conjugated, either with or without a linker. In one embodiment, the chemotherapeutic agent is a DNA synthesis inhibitor or a microtubule inhibitor. In one embodiment, the DNA synthesis inhibitor is cytarabine or another deoxycytidine analogue as described herein. In one embodiment, the DNA synthesis inhibitor is a DNA elongation terminators and functions in a similar way to cytarabine such as fludarabine, nelarabine, cladribine, or clofarabine. In one embodiment, the dopamine receptor antagonist is a $D_2$ family dopamine receptor antagonist. In one embodiment, the composition comprises a dopamine receptor antagonist selected from Table 1. In one embodiment, the dopamine receptor antagonist is a phenothiazine derivative such as thioridazine. In one embodiment, the dopamine receptor antagonist is a antibody selective for one or more dopamine receptors. Optionally, the compositions described herein include a pharmaceutically acceptable carrier such as those described in Remington's Pharmaceutical Sciences (2003-20th edition) and in The United States Pharmacopeia: The National Formulary (USP 24 NF19) published in 1999. In one embodiment, there is provided a composition comprising thiorodazine, cytarabine and a pharmaceutically acceptable carrier.

In one embodiment, the chemotherapeutic agent and the DR antagonist and directly bonded, such as through a covalent bond between an atom that is part of the chemotherapeutic agent and an atom that is part of the DR antagonist. Optionally, the chemotherapeutic agent and the DR antagonist are conjugated through a linker. In one embodiment the chemotherapeutic agent and the DR antagonist are conjugated through a linker. As used herein, the term "linker" refers to a moiety of one or more atoms that serves to bind or couple the chemotherapeutic agent and the DR antagonist. Examples of linkers include, but are not limited to, polymers such as polyethylene glycols, polypropylene glycols, polyvinyl alcohols and/or polyvinyylpyrolidones.

A further aspect of the disclosure includes the use of a dopamine receptor antagonist and a chemotherapeutic agent for the treatment of cancer or a precancerous disorder or the use of a composition comprising a dopamine receptor antagonist and a chemotherapeutic agent for the treatment of cancer or a precancerous disorder. In one embodiment the cancer is leukemia. In one embodiment, the leukemia is acute myeloid leukemia or monocytic leukemia. In one embodiment, the dopamine receptor antagonist is a phenothiazine derivative such thioridazine, chlorpromazine, fluphenazine, or prochlorperazine. In one embodiment, the DR antagonist is selected from the compounds listed in Table 1. In one embodiment, the DR antagonist is an antibody selective for one or more dopamine receptors. In one embodiment, the chemotherapeutic agent is a DNA synthesis inhibitor such as cytarabine or a microtubule inhibitor such as paclitaxel or docetaxel.

The following non-limiting examples are illustrative of the present disclosure:

EXAMPLES

Example 1

Thioridazine is Cytotoxic to Leukemic Cell Lines

The effect of Thioridazine on normalized cell number was evaluated in 3 leukemic cells lines: HL-60, MV4-11 and OCI-AML3. All three lines are leukemic cell lines. HL-60 was derived from promyelocytic AML whereas MV 4-11 and OCI-AML3 are representative of AML. Each compound was incubated with the cells for 72 h. The control was DMSO (i.e. the vehicle used for the compound) for 72 h. Each condition had three replicates.

As shown in FIG. 1, doses of 0.1 µM and 1 µM thioridazine had little effect on normalized cell number, while at 10 µM the normalized cell number was reduced to almost zero.

Example 2

Differential Activity of Thioridazine on AML Blast-Forming Potential and Colony Forming Potential of Normal Stem Cells The effects of thioridazine on blast formation in an AML cell line was compared to the effect of thioridazine on colony formation in normal human stem cells.

Figure 2:
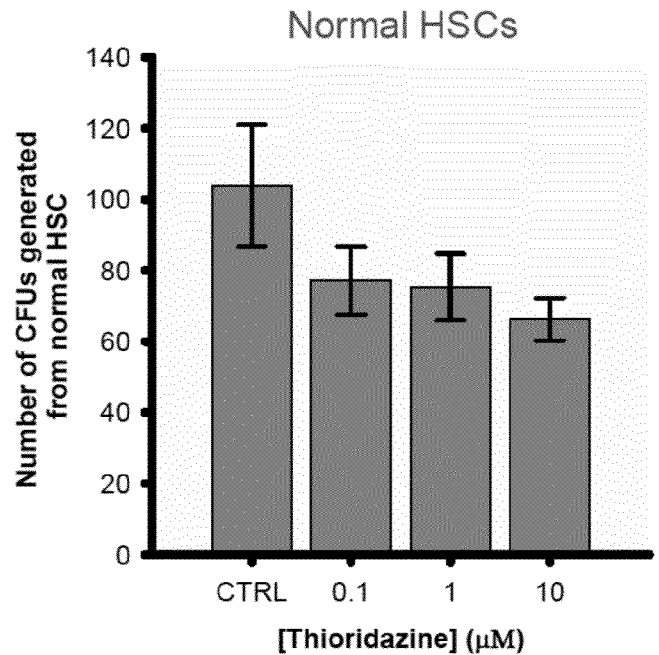
FIG. 2 shows that thioridazine 10 µM has limited affects on the colony forming potential of normal HSCs (2A) while significantly reducing AML blast forming potential.
Figure 2:
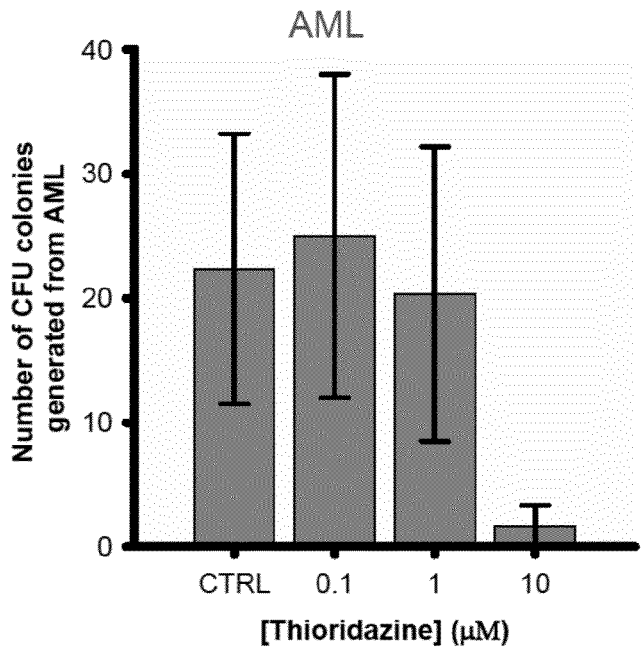

Normal HSCs and progenitors were sourced from either mobilized peripheral blood or umbilical cord blood of health patients. Primary AML cells were taken from patients diagnosed with AML. Both normal HSCs and primary AML cells were cultured under standard in vitro methocellulose assay conditions (see http://www.stemcell.com/en/Products/All-Products/MethoCult-H4434-Classic.aspx as well as Clinton Campbell et al. The human stem cell hierarchy is defined by a functional dependence on Mcl-1 for self-renewal capacity. Blood 116 (9) 1433-1442 (Jun. 4, 2010), hereby incorporated by reference) for at least 14 days before the number of colonies were recorded. As shown in FIG. 2, 10 µM thioridazine has a differential effect on normal HSCs versus AML cells. 10 µM thioridazine reduced the colony forming potential of normal HSCs from about 100 (CTRL treated with DMSO) to about 66 total colonies (FIG. 2A), but had a much more significant effect on AML cells reducing the number of CFU colonies to about 22 blast colonies (FIG. 2B) to 1.6 blast colonies.

Figure 3:
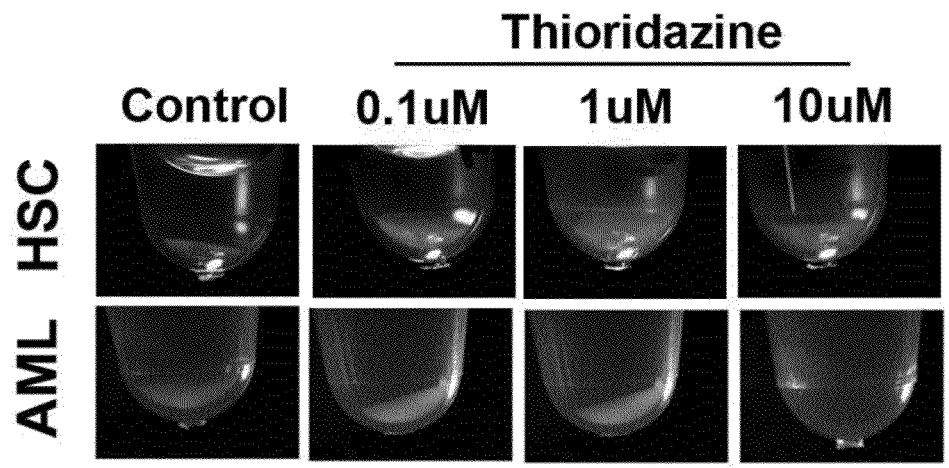
FIG. 3 shows cell pellets of CFU colonies generated from normal HSC and AML treated with Thioridazine.

FIG. 3 shows cell pellets of CFU colonies generated from normal HSC and AML treated with thioridazine. At a dose of 10 µM, pelleted cells are still visible for HSCs, but not for AML cells. Thioridazine therefore selectively targets Blast-CFU Potential of AML cells.

Example 3

Chlorpromazine is Toxic to AML Cell Lines

Figure 4:
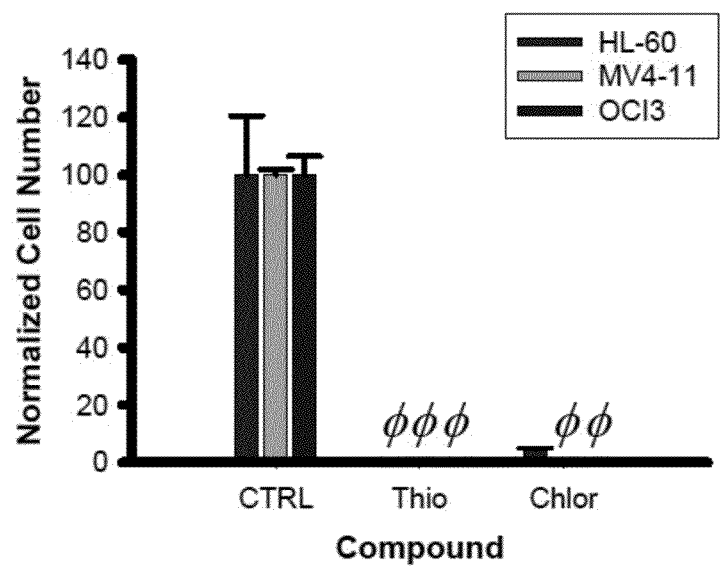
FIG. 4 shows that both 10 µM chlorpromazine and 10 µM thioridazine is cytotoxic to leukemic cell lines HL-60, MV4-11 and OCI3.

The dopamine receptor antagonist and phenothiazine-related compound chlorpromazine was also investigated for effects on the AML cell lines HL-60, MV4-11 and OCI-AML3. Testing was performed as set out in Example 1. As shown in FIG. 4, 10 µM Chlorpromazine is toxic to AML cell lines.

Example 4

Expression of Dopamine Receptors in Normal Blood Versus Leukemia

The expression of the dopamine receptors DR1, DR2, DR3, DR4 and DR5 were analyzed in AML cell lines HL-60, MV4-11, AML-oCl2 and AML-OCI3), Primary AML cells (AML22101, AML29428, AML22174, AML29560) isolated from AML patients, normal blood mononuclear cells (MNC) (MPB21471 and MPB28137; healthy patient blood) as well as umbilical cord blood primary cells enriched for normal Human Stem Cells or progenitors (CB107, CB108 and CB109) using StemSep® Human Hematopoieitc Progenitor Cell enrichment kit (http://www.stemcell.com/en/Products/All-Products/StemSep-Human-Hematopoietic-Progenitor-Cell-Enrichment-Kit.aspx) and enrichment levels of HSCs/Human Progenitor cells confirmed by flow cytometry. Isotype expression was measured as background. Peaks to the right of the isotype peak represent positive expression of DR markers.

Figure 5:
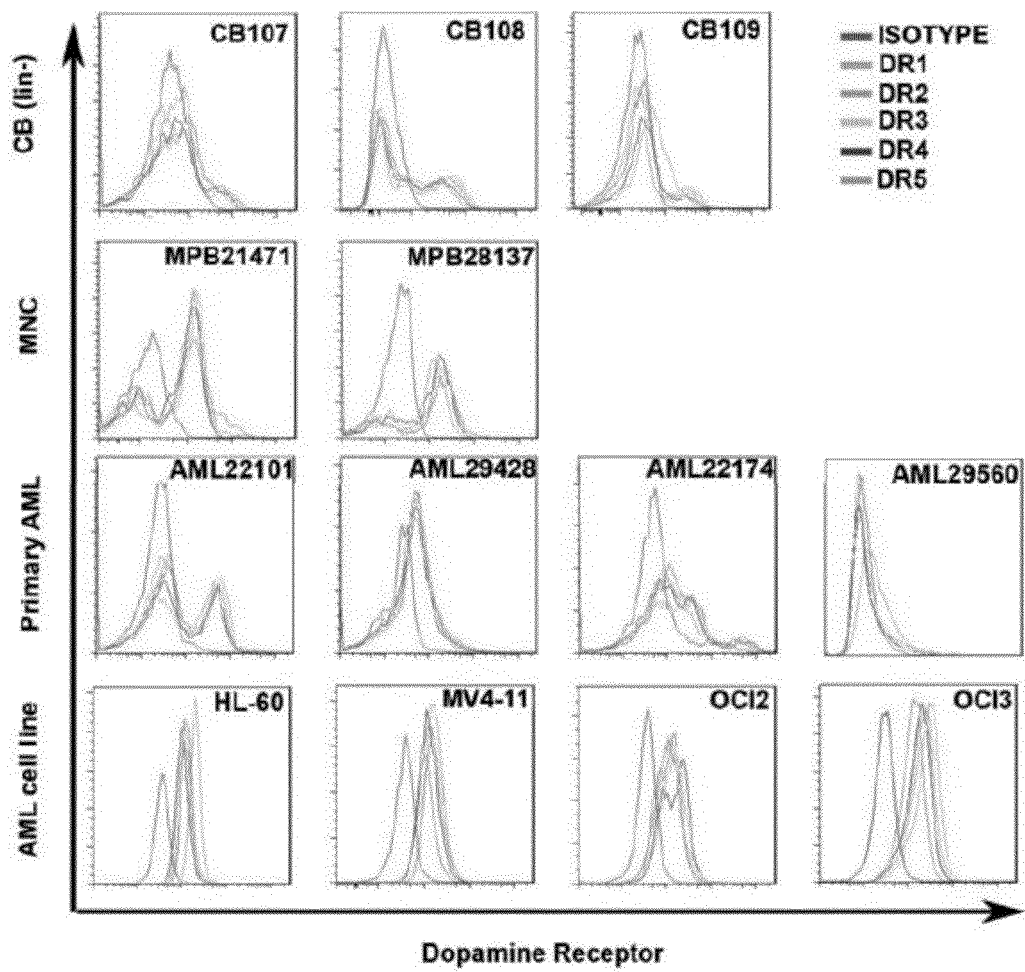
FIG. 5 shows the expression of dopamine receptors DR1, DR2, DR3, DR4 and DR5. DR expression was observed in AML cell lines, some primary AML and mononuclear cells (MNC) but not in HSC enriched cells (CB lin(−)).

As shown in FIG. 5, dopamine receptors are expressed on primary AML, AML cell lines and normal mononuclear blood cells (MNC) but not in blood enriched for normal HSCs (CB(lin–). The data shows that when the sample is positive for DR expression that all five DR subtypes are usually present.

Not all primary AMLs were observed to express dopamine receptors. Accordingly, subjects may be pre-screened for the expression of dopamine receptors in order to identify subjects suitable for AML treatment with DR antagonists. Optionally, pre-screening of subjects may encompass all five DR subtypes, or specific subtypes or combination of subtypes.

Example 5

Multiple DR Antagonists are Cytotoxic to AML Cell Lines

A series of dopamine receptor agonists, $D_{3-}$ antagonists, $DR_{1\ \&\ 5}$-antagonists and multi-receptor antagonists were tested for cytotoxicity against three AML cell lines HL-60, OCI-AML2 and OCI-AML3. Testing was performed as set out in Example 1.

Figure 6:
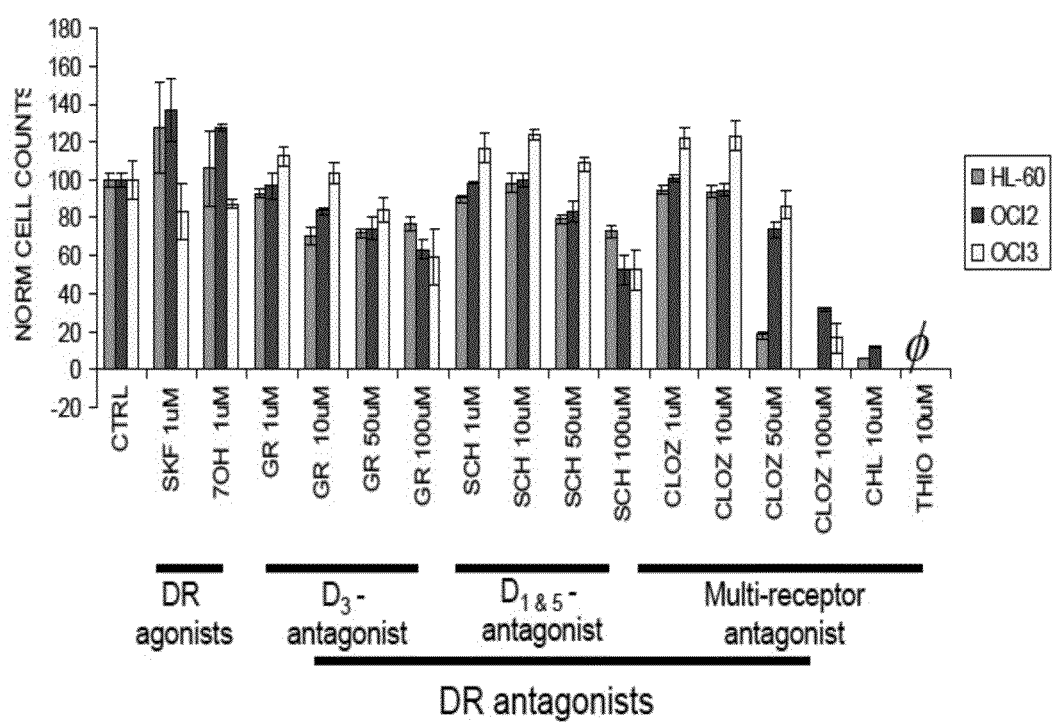
FIG. 6 shows that multiple DR antagonists are cytotoxic to AML cell lines. SKF=(R)-(+)-SKF-38393 hydrochloride; 7OH=R(+)-7-Hydroxy-DPAT hydrobromide; GR=GR 103691; SCH=R(+)-SCH-23390 hydrochloride; CLOZ=Clozapine; CHL=Chlorpromazine hydrochloride; THIO=Thioridazine.

As shown in FIG. 6, CLOZ at higher concentrations as well as CHL and THIO have a significant effect on cytotoxicity of AML cell lines. Without being limited by theory, the cytotoxic effect may require inhibition of multiple dopamine receptors. THIO, CHL and CLOZ being multireceptor antagonists work to eradicate the AML cell lines while the $D_3$ and $DR_{1\ \&\ 5}$-specific antagonists only reduce cell count to 60%.

Example 6

Dopamine Receptors are Expressed in the CD14+ Cell Population of Primary AML The expression of dopamine receptor subtypes was analyzed in primary AML cells. Primary AML cells obtained from AML patients were co-stained with antibodies specific to the DR subtype and CD14 prior to being analyzed using flow cytometry. The majority of DR+ cells were found to be positive for CD14.

Figure 7:
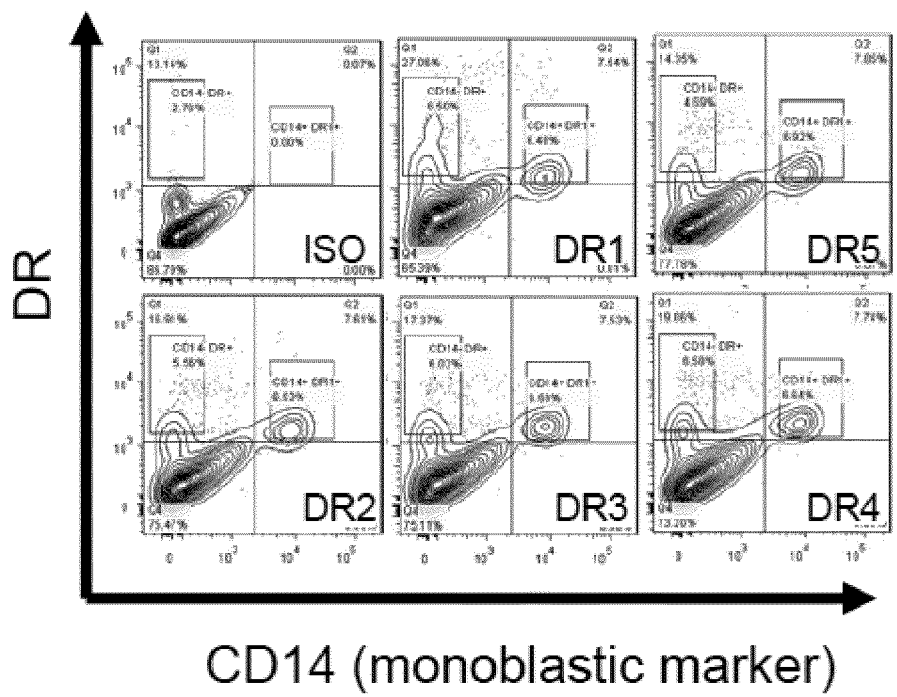
FIG. 7 shows FACS data showing that dopamine receptors are expressed in the population of CD14+ cells in primary AML.

As shown in FIG. 7, the expression of the CD14 monocytic marker is correlated with the expression of each DR subtype.

The effects of thioridazine were also examined on a subpopulation of CD14+ cells in primary AML. Primary AML cells were cultured under control (DMSO vehicle) or 10 uM thioridazine for 72 h and then stained for with antibodies specific to CD14. The number of CD14+ cells in both control and thioridazine treated samples was determined using flow cytometry and the frequency of CD14+ cells was found to be lower in the thioridazine treated sample, suggesting that this compound selectively targets the CD14+ subpopulation in AML cells.

Figure 8:
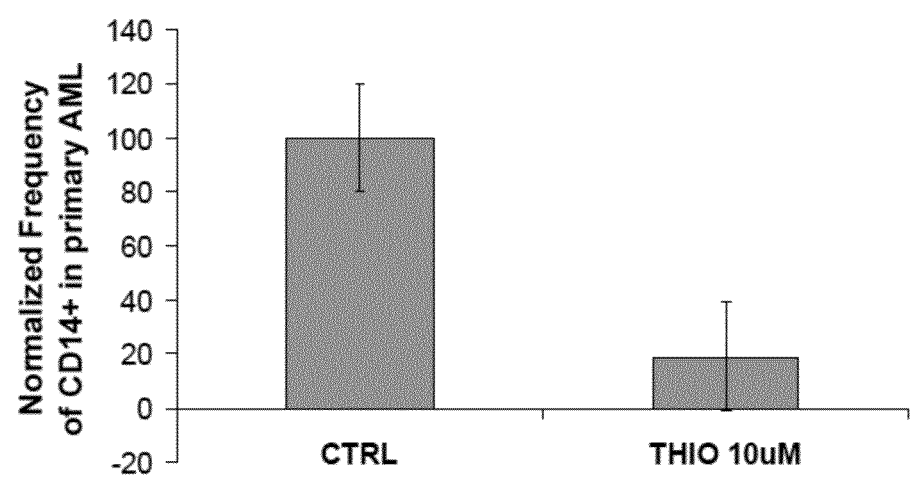
FIG. 8 shows that thioridazine selectively targets and reduces the normalized frequency of CD14+ cells in primary AML.

As shown in FIG. 8, 10 µM thioridazine also reduced the normalized frequency of CD14+ cells in primary AML cells, showing that thioridazine selectively targets CD14+ cells. The AML control group contained a fraction of CD14+ cells. This fraction is reduced with thioridazine treatment and is represented as a reduction in the normalized frequency of the control (100%) versus treated (20%).

Example 7

Identification and Characterization of Drugs that Induce Differentiation of hPSCs Identification of drugs that target cancer stem cells (CSCs) without affecting normal stem cells (SCs) would be ideal for future cancer therapies, but is limited by the lack of assays for both CSCs and normal SCs in the human that are amenable to robust biological screens. As set out in the following examples, using a neoplastic vs. normal human pluripotent stem cell (hPSC) differentiation platform, compounds were identified that are not toxic, but induce differentiation to overcome neoplastic self-renewal of CSCs. Of the several candidate anti-CSC agents identified, thioridazine, an approved anti-psychotic drug, was able to selectively target human somatic CSCs capable of in vivo leukemic disease initiation while having no effect on normal blood SC capacity. Antagonism of dopamine receptor (DR) signaling by thioridazine forms the basis of selective CSC targeting, and revealed DR as a biomarker for CSCs of hematopoietic origin.

Experimental Procedures

Generation of Neoplastic hPSC EOS-GFP Lines.

Neoplastic v1H9 or v2H9 hPSC cells (Werbowetski-Ogilvie et al., 2009) were transduced with lentivirus bearing the EOS-C3+ or EOS-S4+ vectors provided by Dr James Ellis (Hotta et al., 2009). After lentiviral transduction cells were selected using Puromycin, and subsequently sorted as single cells into a 96-well plate based on GFP expression using a FASCAria II (Becton-Dickinson). Colonies generated from single cell clones were used to establish the v1H9-Oct4-GFP (EOS-C3+), v2H9-Oct4-GFP (EOS-C3+) and v1H9-Sox2-GFP (EOS-S4+) lines.

Cell Culture.

The H9 hESC, v1H9, v1H9-Oct4-GFP, v2H9-Oct4-GFP, v1H9-Sox2-GFP and fibroblast-derived iPSCs were cultured as previously described (Chadwick et al., 2003; Werbowetski-Ogilvie et al., 2009).

Primary Human Samples.

For AML specimens, peripheral blood and/or bone marrow was collected at the time of clinical presentation. Healthy hematopoietic cells were obtained from umbilical cord blood samples. All samples were obtained following informed consent according to Research Ethics Board approved protocols at McMaster University and the London Health Sciences Centre.

In Vitro Culture Platform for Normal and Neoplastic hPSCs.

Chemical screens involved v1H9-Oct4-GFP cells seeded at 5,000 cells per well in mouse embryonic fibroblast conditioned media (MEFCM) supplemented with 8 ng/ml bFGF. 24 hours later the media was exchanged for MEFCM with compounds at 10 µM and 0.1% DMSO, 0.1% DMSO (−BMP4) or 100 ng/ml of BMP4 and 0.1% DMSO (+BMP4) for 48 hours before being exchanged with fresh media with compound for a further 24 h (total compound treatment time 72 h) prior to being fixed and prepared for automated imaging and plate reader analysis. Confluent H9 & fibroblast-derived iPSC were seeded at 10,000 cells per well in MEFCM supplemented with 8 ng/ml bFGF. 24 hours later the cells were treated with compounds at 10 µM and 0.1% DMSO, 0.1% DMSO (−BMP4) or 100 ng/ml of BMP4 and 0.1% DMSO (+BMP4). Fresh MEFCM supplemented with compounds was exchanged daily for 5 days. On day 5, hPSC's were fixed and prepared for automated imaging and plate reader analysis. See supplementary experimental procedures for further details.

Teratoma Assay.

400,000 H9 hESCs or v1H9-Oct4-GFP were injected intra-testicularly into male NOD/SCID mice and teratomas analyzed for Oct4 as previously described. (Werbowetski-Ogilvie et al., 2009).

Xenotransplantation Assays.

NOD.Cg-Prkdc$^{scid}$ Il2rg$^{tm1 Wji}$/SzJ adult mice (NSG) were sub-lethally irradiated with 315 rads 24 hours prior transplantation. 0.8-1.0×10$^7$ AML MNCs or 1.5-1.8×10$^5$ CB lin-hematopoietic cells treated with compound or DMSO-vehicle for 24 h were injected via tail vein (IV). After 6-10 weeks, animals were culled, and the BM and spleen were analyzed for the presence of human cells by flow cytometry (LSRII, BD) and data was analyzed using FlowJo software (Tree Star Inc). For secondary HSPC transplants, equal number of engrafted human cells from CB lin– transplants were injected IV in adult irradiated NSG mice as described for primary transplants.

Statistical Analysis.

Data is represented as the mean±SEM or mean±SD. Significant differences between groups were determined using unpaired two-way or one-way Students' t test.

Pluripotent Stem Cell Culture.

The H9 hESC, v1H9, v1H9-Oct4-GFP, v2H9-Oct4-GFP, v1H9-Sox2-GFP and fibroblast-derived iPSCs were cultured on Matrigel™-coated (BD Biosciences 353234) plates with mouse embryonic fibroblast-conditioned (MEFCM) media supplemented with 8 ng/ml bFGF (GIBCO 13256-029). MEFCM is composed of KO-DMEM (GIBCO 10829-018), 20% KO-Serum Replacement (GIBCO 10828-028), 1% Non-Essential Amino Acids (GIBCO 11140-050), 1 mM L-Glutamine, 0.1 mM β-mercaptoethanol (Sigma Aldrich M7522). Cell lines were passaged every 7 days using 100 Units/mL of Collagenase IV (GIBCO 17104-019) for 2-3 minutes. Cell seeding density, assay duration and DMSO vehicle concentration in 96 wells were optimized for v1H9-Oct4-GFP cells and normal H9 hPSC. For v1H9-Oct4-GFP, an optimum initial seeding density of 5,000 cells per well for 72 h of treatment was selected based on maximal levels of GFP and z' discrimination between ±BMP4 controls. For normal hPSC, an optimal seeding density of 10,000 cells per well was selected based on maximal z'-prime discrimination between ±BMP4 controls.

Primary Human Samples.

Mononuclear cells were prepared using Ficoll-Paque Premium (GE Healthcare). For hematopoietic cells, lineage depletion was performed using EasySep (StemCell Technologies) following manufacturer's recommendations.

AML/HPSC Cell Culture.

AML cell lines, namely, OCI-AML2 (M4), OCI-AML3 (M4), HL-60 (M2) and MV-4-11 (M5) were cultured in RPMI (Gibco) supplemented with 5% heated-inactivated FBS (Hy-Clone). For DR agonist studies with R(+)-7-Hydroxy-DPAT hydrobromide (Sigma), serum-free conditions were employed instead due to the prevalence of dopamine in FBS (Little et al., 2002). AML patient blasts were cultured in IMDM supplemented with 5% heated inactivated FBS (Hy-Clone), 5 ng/mL IL3 (R&D systems), $5 \times 10^{-5}$ M β-mercaptoethanol (Sigma) and BIT (StemCell Technologies). HSC media contained IMDM supplemented with 1% BSA (Sigma), 100 ng/mL SCF (R&D systems), 100 ng/mL Flt-3L (R&D systems) and 20 ng/mL TPO (R&D systems). Patient HSPC and AML samples were treated with compound or DMSO-vehicle (0.1%) for 24 h prior to CFU plating or xenotransplantation studies.

Antibodies.

Antibodies used for immunocytochemistry were the following: Oct3/4 (BD Trunsduction Laboratories, cat#611203), Sox2 (R&D, cat#AF2018). To detect human hematopoietic cells, Pacific Blue-, PE-, APC- or FITC labeled anti-human CD45 was used (BD Biosciences). FITC anti-CD33, PE anti-CD13, FITC anti-CD41a, FITC anti-HLA DR, and PE anti-CD19 antibodies were obtained from BD Pharmingen. PE anti-CD14, PE anti-CD15 and PE anti-GlyA were acquired from Immunotech Beckman Coulter. To determine pluripotency, PE anti-SSEA3 (BD Biosciences) and PE- or AlexaFluor488 anti-Oct4 (BD Biosciences). Rabbit anti-human dopamine receptor antibodies; DRD1 (Cat#324390), DRD2 (Cat#324393), DRD3 (Cat#324402), DRD4 (Cat#324405) and DRD5 (Cat#324408) were sourced from EMD Chemical. Anti-rabbit Alexa-Fluor-488 (Molecular Probes) was used as the secondary antibody. Primary anti-p53 (Cat#2527) and anti-p21 (Cat#2947) rabbit IgG sourced from Cell Signaling Technology were used to stain fixed and permeabilized cells. Anti-rabbit alexa-Fluor-546 (Molecular Probes) was used as the secondary antibody.

Automated Imaging and Analysis

Imaging Neoplastic hPSC.

Cells were fixed in 2% paraformaldehyde and stained with 10 µg/mL Hoechst 33342 (Invitrogen) with a Combi Multi-drop Dispenser (Thermo). For experiments that involved Oct4 immunocytochemistry, a monoclonal antibody for Oct4 (BD) was used along with an Alexa-Fluor-647 secondary (Invitrogen). Immunocytochemical staining was performed by a Janus automated liquid handler (Perkin Elmer). Images were acquired at 10× N.A with an Arrayscan HCS VTI Reader (Cellomics) by means of epi-fluorescence illumination and standard filter sets.

Imaging Normal hPSC.

Cells were fixed in 2% paraformaldehyde and stained with 10 µg/mL Hoechst 33342 (Invitrogen). Standard fluorescence immunocytochemical techniques were used to stain the cells with a monoclonal antibody for Oct4 (BD), and an Alexa-Fluor-647 secondary antibody (Invitrogen). All steps were performed by a Janus automated liquid handler (Perkin Elmer). Images were acquired at 5× with an Arrayscan HCS Reader (Cellomics) by means of epi-fluorescence illumination and standard filter sets.

Image Analysis.

Image analysis was performed using custom scripts in Acapella software (Perkin Elmer). Nuclear objects were segmented from the Hoechst signal. For neoplastic cell lines, object intensity analysis was performed on GFP positive cells only. For normal cell lines, the fraction of Alexa-Fluor-647-positive cells was quantified. Images and well-level data were stored and analysed in a Columbus Database (Perkin Elmer) and further data analysis, compounds registration and hit identification in ActivityBase (IDBS).

Gene Expression Analysis.

Cells in specific conditions were collected and RNA was extracted by using RNeasy kit (Qiagen), complementary DNA (cDNA) generation by using SuperScript III® cDNA synthesis kit (Invitrogen), pre-amplification and TaqMan® array reaction (Applied Biosystems) were performed according to manufacturer's instructions. The gene expression profile for each treated cell population was analyzed using TaqMan® Stem Cell Pluripotency Array Card on ViiA 7 Real-Time PCR System (Applied Biosystems). Each reaction sample was dispensed into loading wells on the array card and centrifuged twice at 336×g for 1 min each time, sealed, and placed in the thermal cycler. The following cycling conditions were used for all array card applications: 45° C. for 10 min, 94° C. for 10 min, and 40 cycles of 94° C. for 30s followed by 60° C. for 1 min. Array data were normalized to 18S RNA and GAPDH and comparisons were performed using data analysis 2.0 software (Applied Biosystems).

Methylcellulose Colony-Forming Assay.

AML patient or CB lin– cells were cultured 24 hours in the presence of compound or DMSO-vehicle (0.1%) control. AML cells were plated at 50 000 cells/mL in Methocult GF H4434 (Stem Cell Technologies). CB lin– cells were plated at 1000 cells/mL in Methocult GF H4434 (Stem Cell Technologies). Colonies were scored after 14 days of culture using standard morphological criteria.

Volumetric Cell Counting.

The number of AML-OCI2 and AML-OCI3 cells present after 72 h treatment with DR antagonists (FIG. 16b) and agonist (FIG. 16c-d) were counted by measuring the number of events within a fixed volume following the grating strategy defined by forward scatter and side scatter clustering, 7AAD− and Hoechst+.

Example 8

High Throughput Screening Identification of Compounds that Induce Differentiation of Neoplastic hPSCs The inventors have previously described a variant human pluripotent stem cell (hPSC) line that displays neoplastic features which include enhanced self-renewal and survival, along with aberrant block in terminal differentiation capacity in vitro and in vivo (Werbowetski-Ogilvie et al., 2009). Based on these similarities in functional properties to somatic CSCs, neoplastic hPSCs were examined as a surrogate for somatic CSCs that would be amenable for high content and high throughput screening in vitro. A screening platform was developed to identify small molecules that selectively target neoplastic hPSCs whilst having little effect on normal hPSCs. This differential screening platform is capable of identifying potent candidate drugs that selectively target somatic CSCs while sparing healthy SC capacity.

Oct4 and Sox2 provide a reliable indicator of loss of self-renewing pluripotent state and differentiation induction of normal and neoplastic hPSCs. To provide a more straightforward method for detecting loss of Oct4 or Sox2 during induced differentiation of neoplastic hPSCs, GFP-reporter lines were generated by transduction of neoplastic hPSCs with the EOS-GFP reporter (v1H9-Oct4-GFP and v1H9-Sox2-GFP, respectively) (Hotta et al., 2009). GFP intensity was observed to be correlated with Oct4 and Sox2 expression in treatments that favored self-renewal stability and conditions that induce differentiation with the addition of BMP4. This response was consistently found using an additional neoplastic hPSC line, v2H9 (Werbowetski-Ogilvie et al., 2009) transduced with the same EOSlentivirus GFP-reporter (v2H9-Oct4-GFP), as well as a Sox2 reporter line (v1H9-Sox2-GFP).

The uniform response to differentiation and maintenance of pluripotency in all hPSC cell lines generated also revealed that viral integration or clonal selection by EOS reporter construct insertion is irrelevant to responsiveness. These results suggest that compounds that induce differentiation can be identified based on the reduction of GFP intensity in neoplastic hPSC reporter lines and could be exploited for chemical screening. To that end, conditions for automated high content microscopy and fluorimetric-based high throughput screening were used to detect reductions in pluripotency marker expression of hPSCs. Microscopic analysis of normal hPSCs showed that distinct Oct4+ cells are lost following BMP4 treatment. Similarly, the reduction in both GFP and Oct4 due to BMP4 treatment of neoplastic Oct4-GFP hPSCs was quantified by high content microscopy and plate reader-based fluorimetry. To identify ideal candidates for targeting CSCs differentiation of both normal and neoplastic hPSCs in response to compound treatment was assessed in parallel.

Figure 9:
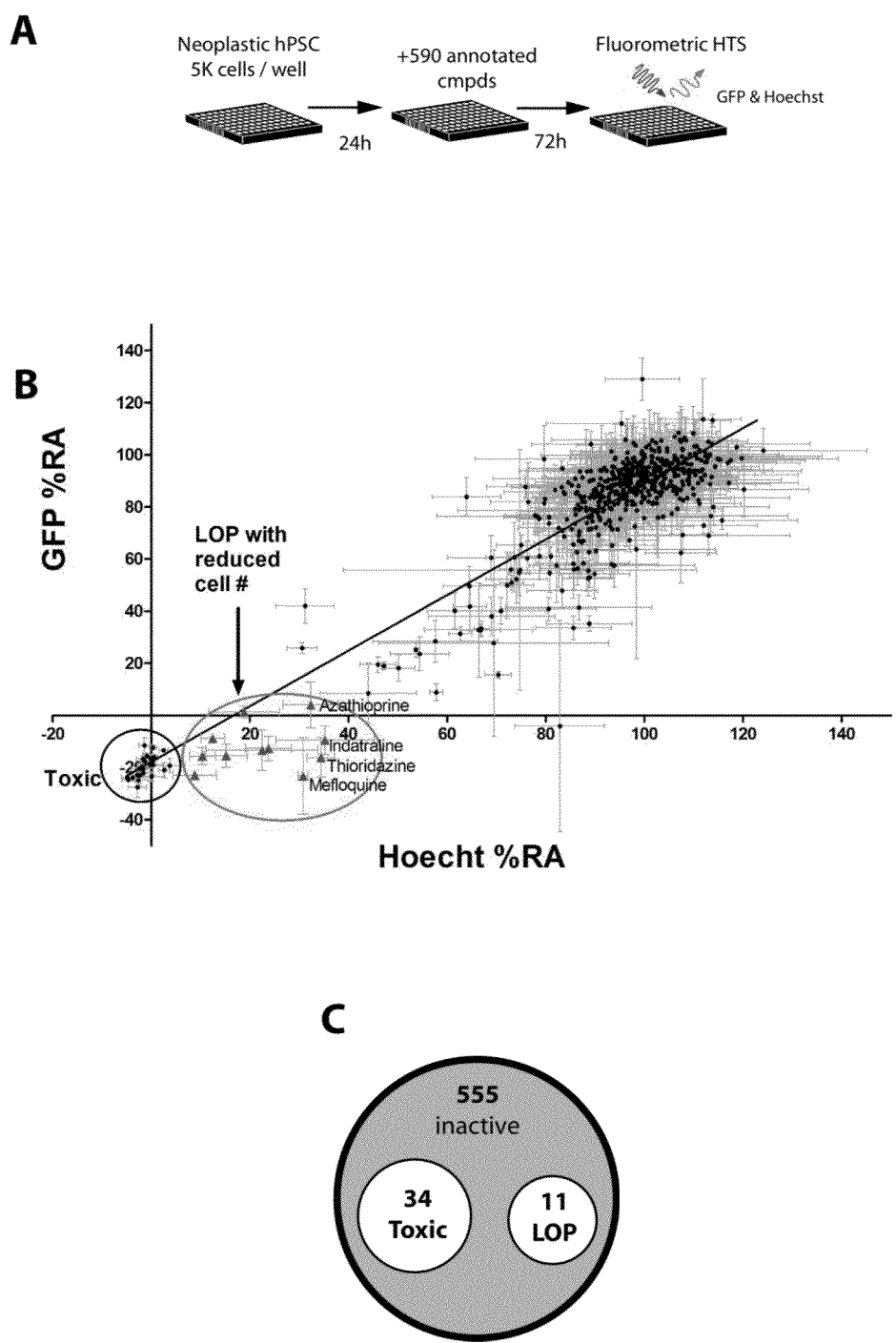
FIG. 9 shows the identification of mefloquine and thioridazine using chemical screening for compounds that differentiate neoplastic hPSC. (A) Schematic of screening strategy. (B) XY-scatter plot of percent residual activity (% RA) of GFP and Hoechst signals of the 590 compound screen. Region outlined demonstrates loss of pluripotency (LOP) as defined by reduced GFP and Hoechst. Each point n=3, mean+/−SD (C) Summary of responses seen with 590 compounds. (D) Chemical structure of candidate compounds; thioridazine, azathioprine and mefloquine. (E) Representative GFP, Hoechst and merged microscopic images of v1H9-Oct4-GFP cells treated with candidate compounds at 10 µM. (F) Histogram of GFP intensity of these images. (G) Dose response curves of v1H9-Oct4-GFP treated with candidate compounds and calculation of $EC_{50}$. Each point n=3; mean+/−SEM.
Figure 9:
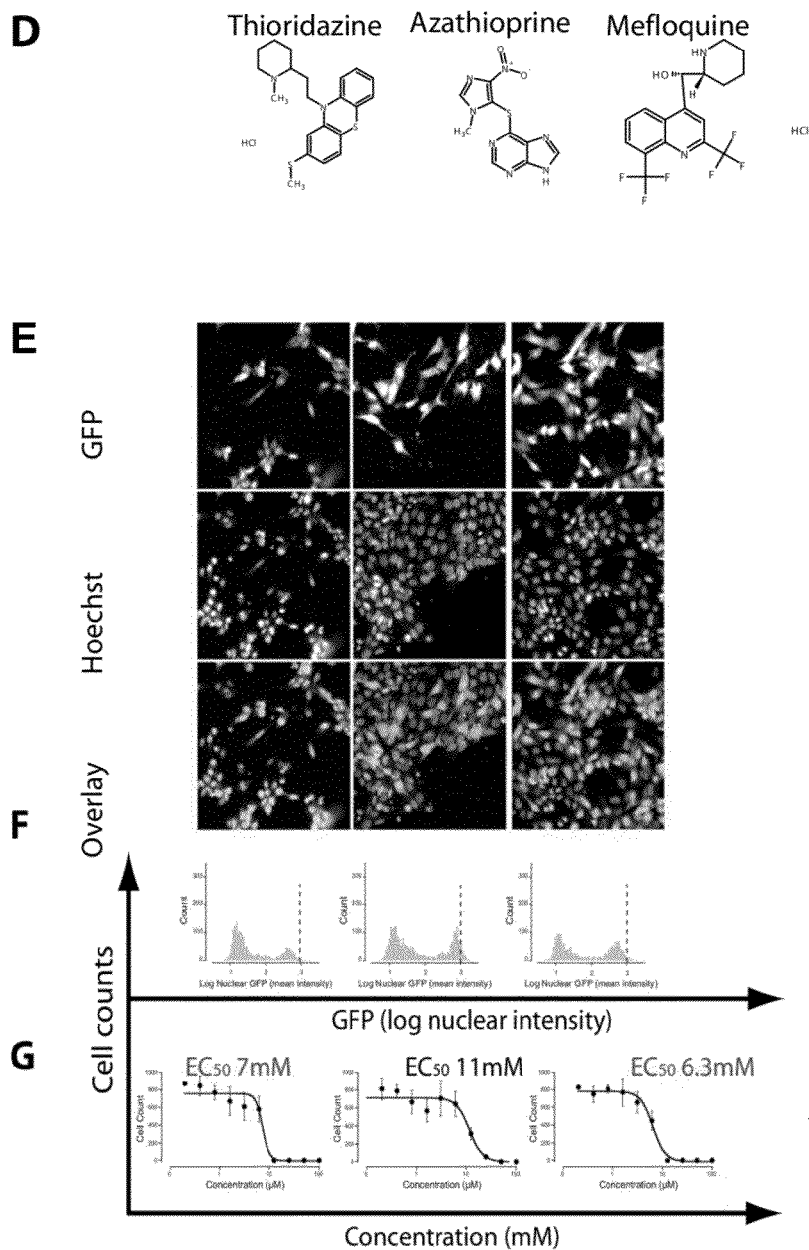

Given the validation of the screening platform a chemical libraries composed of 590 well-established annotated compounds from the NIH Clinical Collection and Canadian Compound Collection was screened. These Collections have been previously scrutinized in numerous other mammalian cell lines (Diallo et al., 2010; Shoemaker, 2006). Following the demonstration that fluorometric highthroughput screening (HTS) and high content screening (HCS) platforms give equivalent measurements for loss of pluripotency (GFP RFU and mean GFP intensity per cell, respectively) and cell count (Hoechst RFU and Cell count, respectively) of the 51 defined compounds, HTS was selected as the preferred platform for more rapidly screening compound libraries (FIG. 9a). Of the 590 compounds screened (at 10 µM based on previous studies (Inglese et al., 2007)), 11 compounds were identified to induce differentiation as indicated by a reduction in both GFP % residual activity (% RA) and Hoechst % RA (FIGS. 9b-c). A total of 4 of these compounds; indatraline, thioridazine, azathioprine, and mefloquine, were identified as candidate compounds based on clustering and levels of Hoechst % RA in excess of 30% (FIG. 9b). Secondary high content analysis revealed indatraline to be a questionable candidate and was thus excluded, whereas content analysis and HTS analyses dually confirmed thioridazine, azathioprine, and mefloquine as candidate compounds (FIG. 9d) and were thus selected for further testing (FIGS. 9e-g). When compared to control-treated hPSCs, each compound appeared to induce distinct morphological changes in neoplastic hPSCs (FIG. 9e). Reduction in GFP intensity was confirmed using image analysis (FIG. 9f) and further assessed over a wide range of doses to calculate half-maximal effective concentration (EC50) for each compound (FIG. 9g). Only thioridazine and mefloquine were found to possess EC50 values lower than the 10 µM target threshold (FIG. 9g) and thus defined as candidates for further in depth evaluation using neoplastic hPSCs and somatic CSCs from patients.

Figure 18:
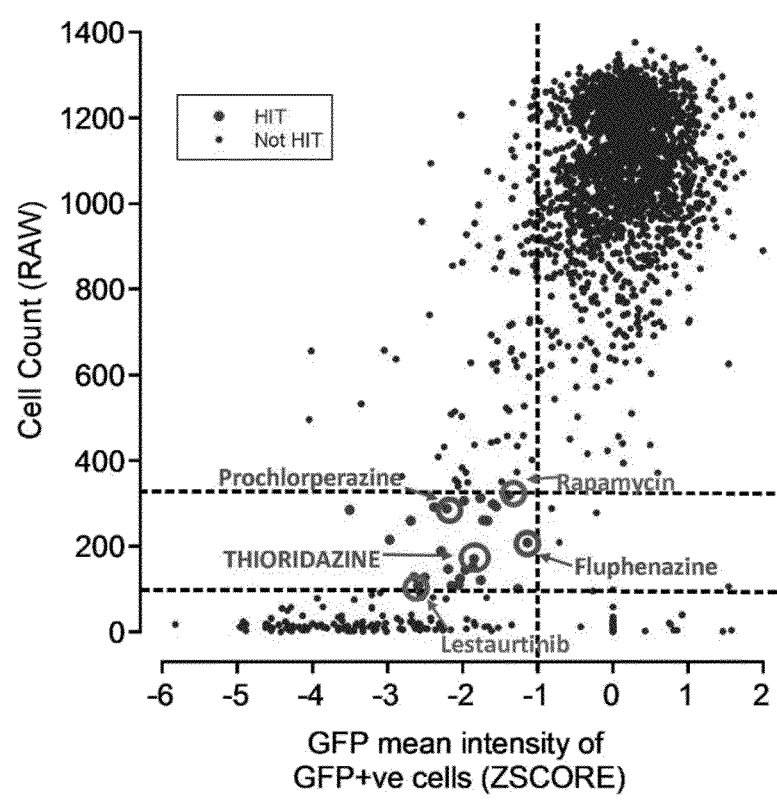
FIG. 18 shows an extended screen that identifies thioridazine-like agents. (A) XY-scatter plot of GFP mean intensity and cell counts of extended screen with 2446 compounds. Region outlined demonstrates loss of pluripotency (LOP) as defined by reduced mean GFP intensity and cell count. Thioridazine's data point is outlined, along with other selected hits. Each point mean of n=3 (B) Chemical structure of other phenothiazine compounds; fluphenazine and prochlorperazine (C) Representative GFP, Hoechst and merged microscopic images of v1H9-Oct4-GFP cells treated with selected hit compounds at 10 µM. (D) Histogram of GFP intensity of these images. (E) Dose response curves of v1H9-Oct4-GFP treated with candidate compounds and calculation of EC50. Each point n=3; mean+/−SEM (F) Fluorescence microscopy of v1H9-Oct4-GFP. GFP, Hoechst, and merged fluorescence images of v1H9-Oct4-GFP cells with or without BMP4 treatment and stained with Hoechst. Corresponding GFP log intensity histograms also shown.
Figure 18:
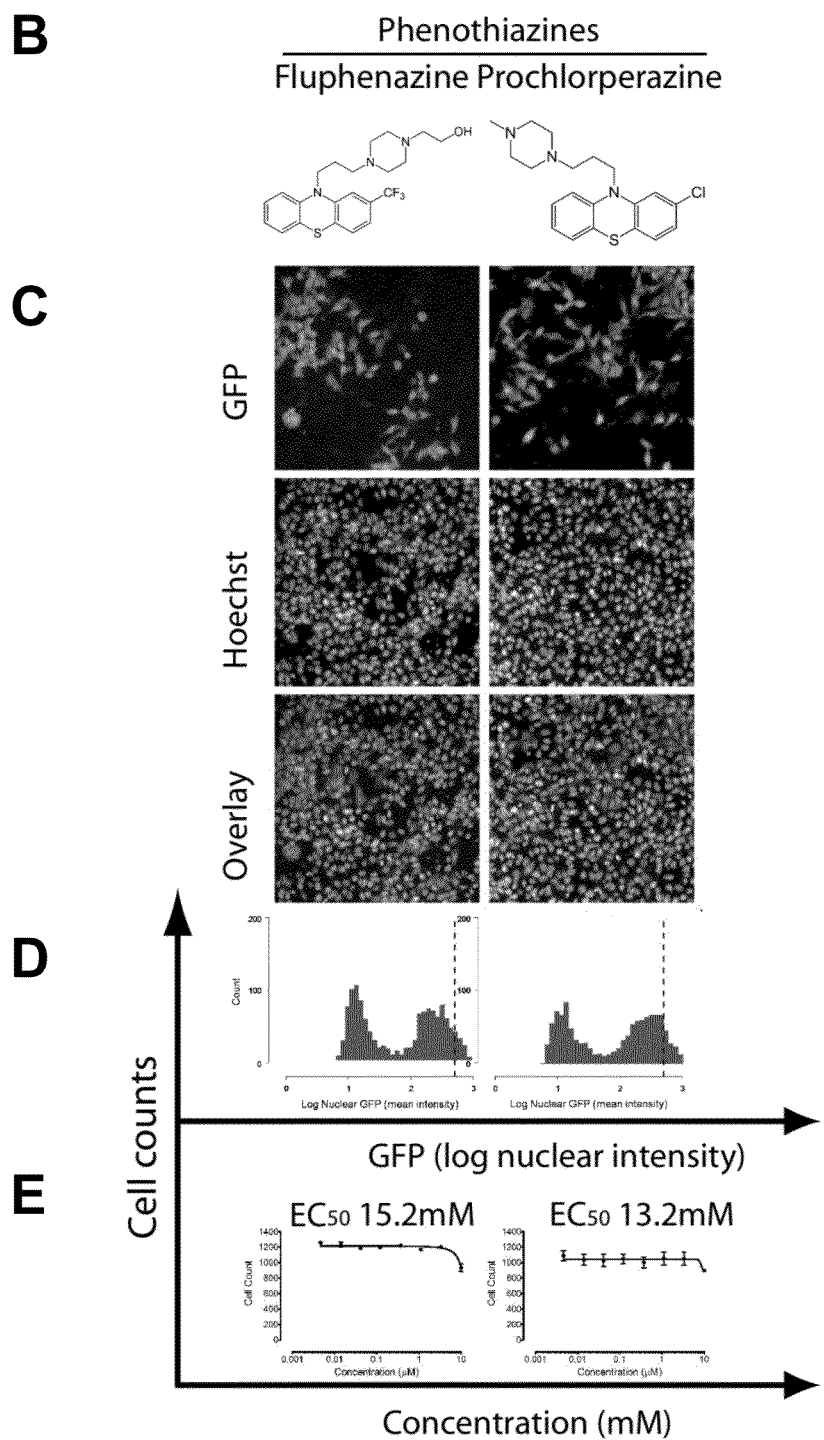
Figure 18:
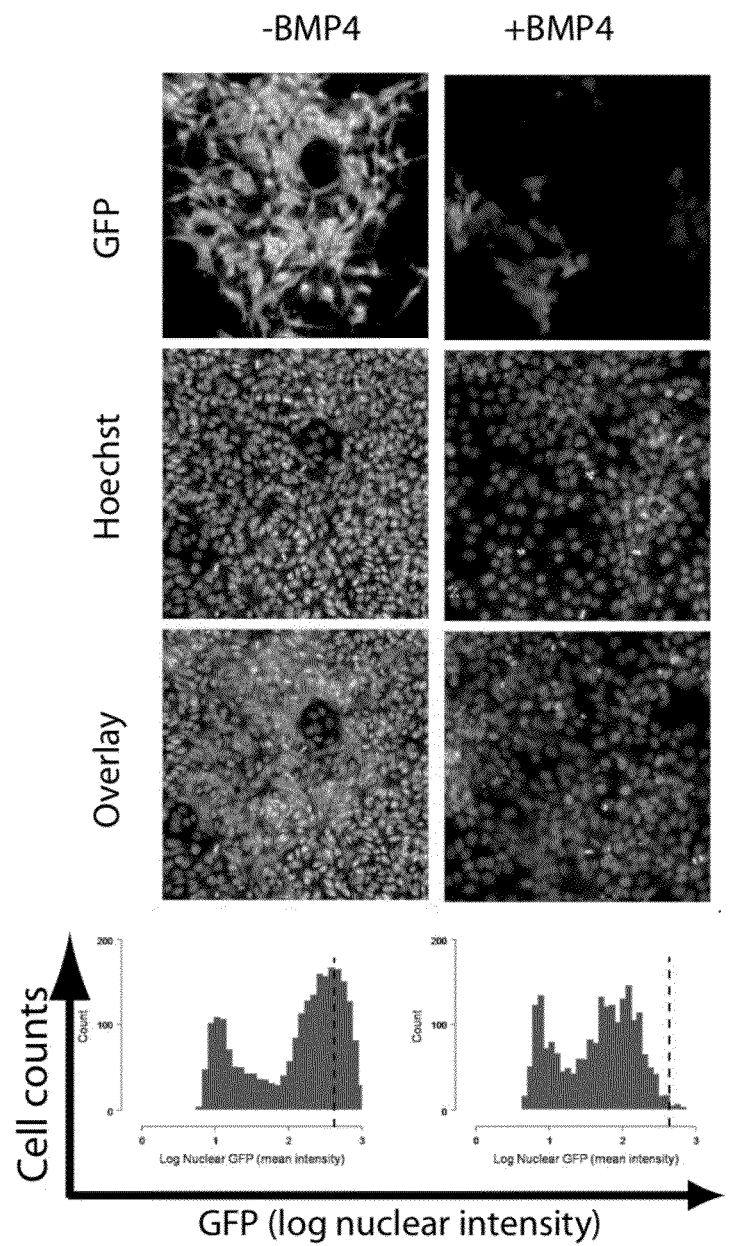

To reaffirm our screening approach and specificity to identify thioridazine-like acting compounds, we expanded the chemical matter used to screen neoplastic hPSC response to include 2446 compounds (FIG. 18a). Thioridazine, along with two other phenothiazine compounds; fluphenazine and prochlorperazine, were identified as hits among a list of 26 compounds identified (FIG. 18a-b). Further assessment of fluphenazine and prochlorperazine using high content analysis revealed distinct morphological changes in neoplastic hPSCs (FIG. 18c) relative to control-treated cells (FIG. 18f). Reduction in GFP intensity was confirmed using image analysis (FIG. 18d) and further assessed over a wide range of doses to calculate EC50 for each compound (FIG. 18e). Of the three phenothiazines identified in the screens, thioridazine exhibited the lowest EC50 in neoplastic hPSCs (FIG. 9g vs. FIG. 18e), making it the best candidate phenothiazine of those tested for targeting of AML CSCs.

Example 9

Figure 10:
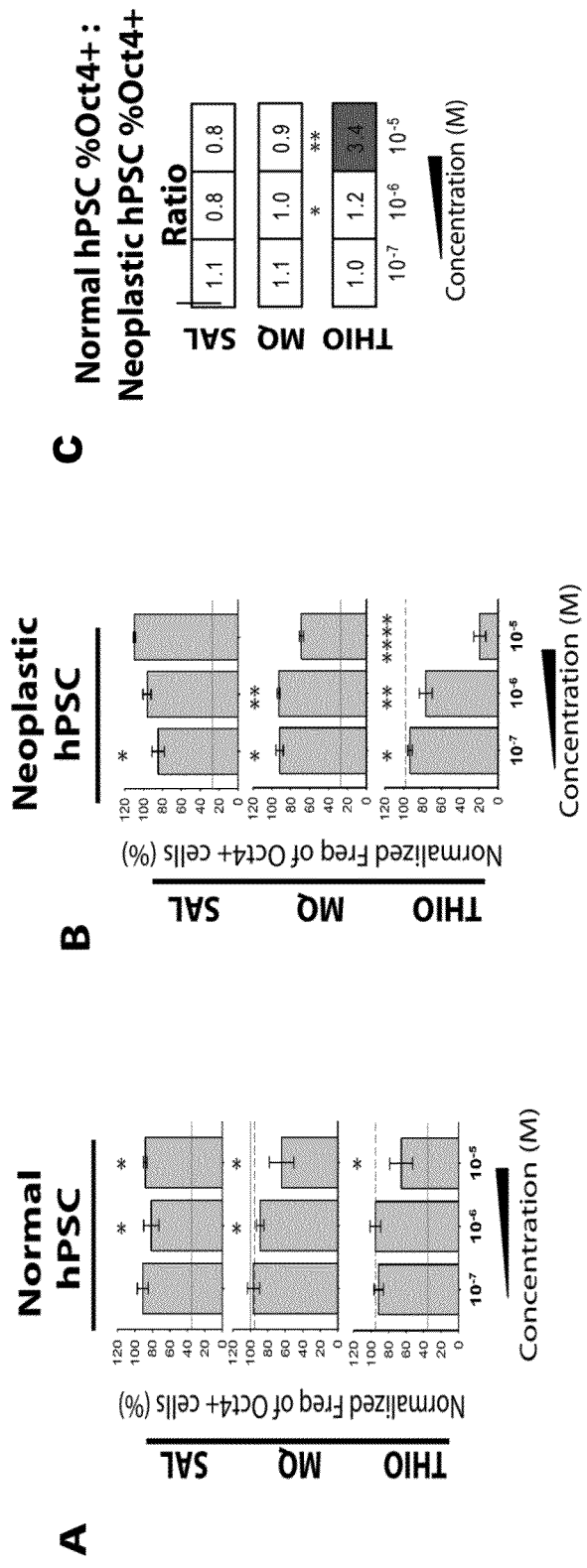
FIG. 10 shows the effect of salinomycin, mefloquine and thioridazine on normal and neoplastic populations. (A-B) Flow cytometry analysis of frequency of Oct4+ cells in (A) H9 and (B) v1H9-Oct4-GFP cells treated with salinomycin (SAL), mefloquine (MQ) and thioridazine (THIO) at $10^{-7}$-$10^{-6}$M. Each bar n=3; mean+/−SD. Values are normalized to DMSO-treated control samples; (−) DMSO mean, (−) mean minus one SD, (−) level of % Oct4+ in BMP4 treated samples. (C) Ratio of normalized % Oct4+ cells in H9 per v1H9-Oct-GFP with same compound at the same concentration. Percent of neoplastic hPSC staining positive for (D) p53 and (E) p21 following 24 h treatment with 10 µM etoposide, 10 µM thioridazine (THIO), BMP4 and DMSO-treated (CTRL) controls. Each bar n=3; mean+/−SD. Representative images of etoposide and thioridazine treated cells included. Arrows show p53+ and p21+ in etoposide-treated cells versus thioridazine-treated cells. (F) Differentiation-associated genes with >2 fold increase following thioridazine treatment of neoplastic hPSC. Genes divided into respective lineages, endoderm (ENDO), mesoderm (MESO), germ cell (GERM), neural (NEURO) and trophoblast (TROPH). Each bar represents the mean of two separate experiments. (G-K) Hematopoietic multilineage and clonogenic potential in response to compound treatment detected using methycellulose assays. Representative colony forming unit (CFU) pellets of (G) hematopoietic stem and progenitor cells (HSPC) versus (H) AML blast CFUs pellets following compound treatment. (I-J) Quantification of respective CFUs and blast-CFUs generated from (I) HSPC and (J) AML blast cells following compound treatment. Values were normalized to DMSO-treated control samples; (−) DMSO mean, (−) mean minus one SEM. Each HSPC bar n=7 individual samples, mean+/−SEM. Each AML bar at least n=5 individual patient samples, mean+/−SEM. (K) Ratio of normalized HSPC CFUs per AML blast CFUs with same compound at the same concentration. (L) Frequency of normalized CD11b granulocytic cells in cultured patient AML cells treated with thioridazine 10 μM (THIO 10 μM) or DMSO vehicle (CTRL) for up to 96 hours. Each bar n=3, mean+/−SD. (*) p<0.05, () p<0.01, (*) p<0.001, (****) p<0.0001.
Figure 10:
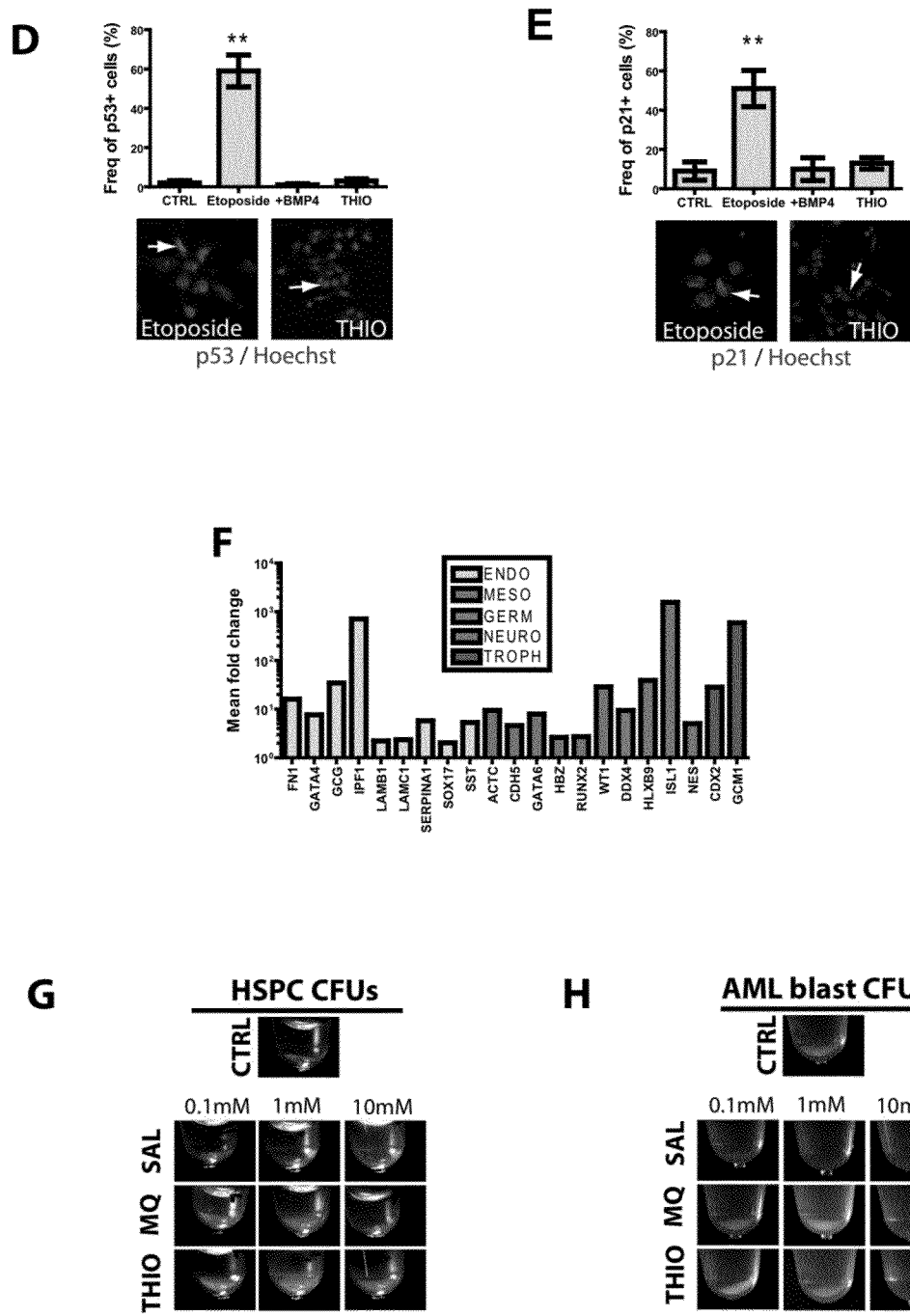
Figure 10:
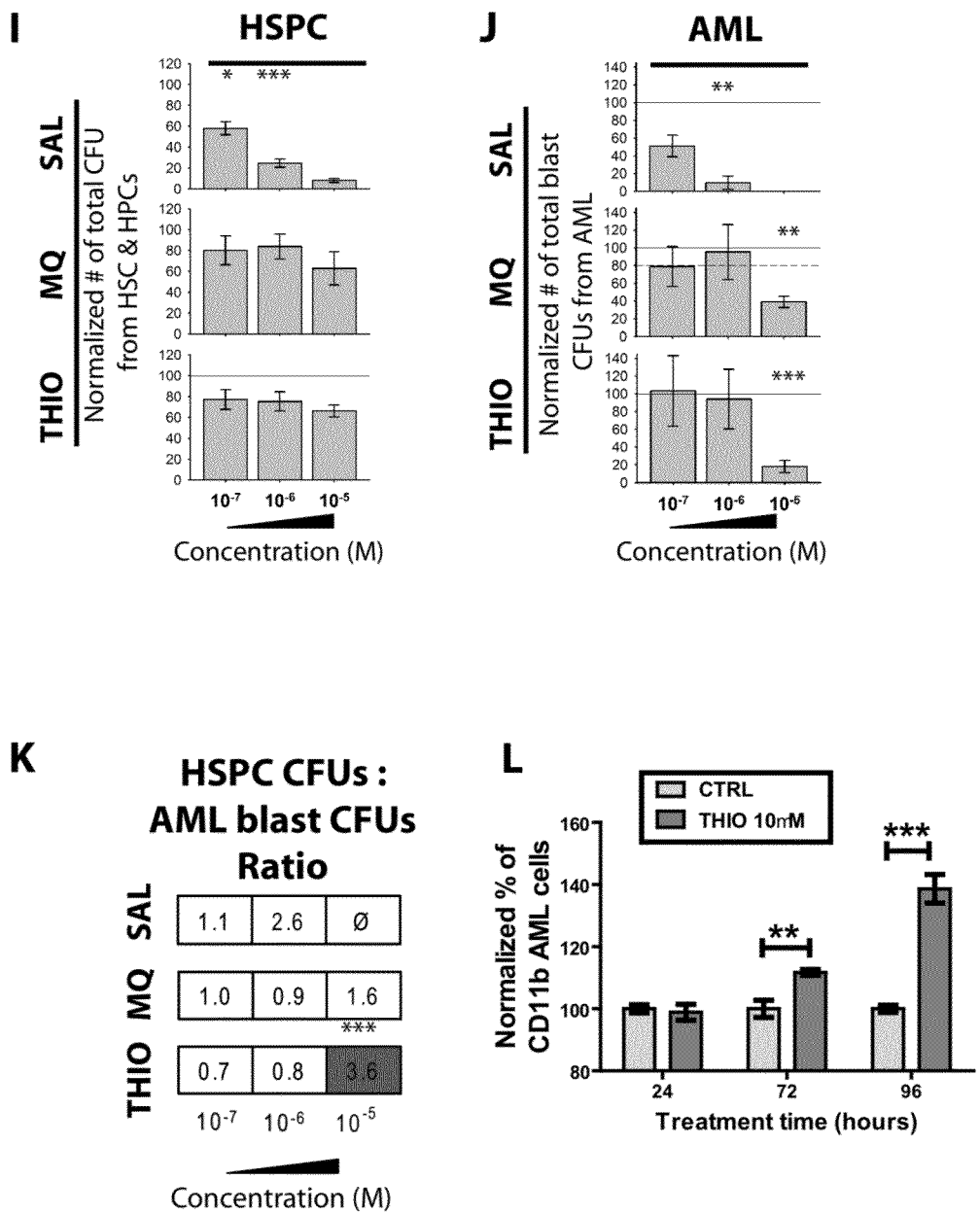
Figure 11:
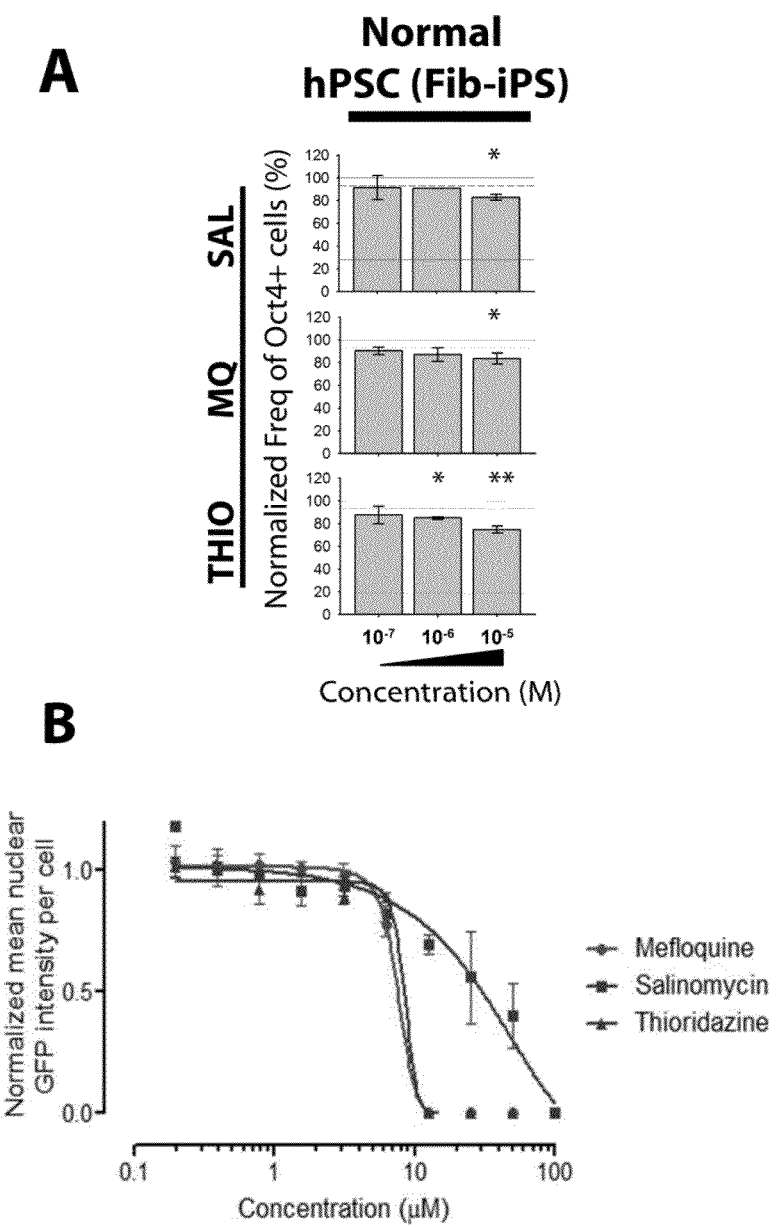
FIG. 11 shows the effect of salinomycin, mefloquine and thioridazine on fibroblast-derived iPSC and HSPC. (A) Flow cytometry analysis of frequency of Oct4+ cells in fibroblast-derived iPSC (Fib-iPS) treated with salinomycin (SAL), mefloquine (MQ) and thioridazine (THIO) at $10^{-7}$-$10^{-6}$M. Each bar n=3; mean+/−SD. Values are normalized to DMSO-treated control samples; (−) DMSO mean, (−) mean minus one SD, (−) level of % Oct4+ in BMP4 treated samples. (B) Extended dose response of compounds on neoplastic hPSC. Each point mean+/−SEM, (C) Hematopoietic lineage potential of CBlin− treated with thioridazine. Colony forming units (CFUs) of erythroblast (CFU-E), macrophage (CFU-M) and granulocyte (CFU-G) colonies generated in methylcellulose assays. (D) Composition of CFU generated from CBlin− treated with salinomycin, mefloquine and thioridazine. Percent composition of CFUs generated with salinomycin (SAL), mefloquine (MQ) and thioridazine (THIO) treatment at 0.1 μM, 1 μM and 10 μM. (*) p<0.05, (**) p<0.01
Figure 11:
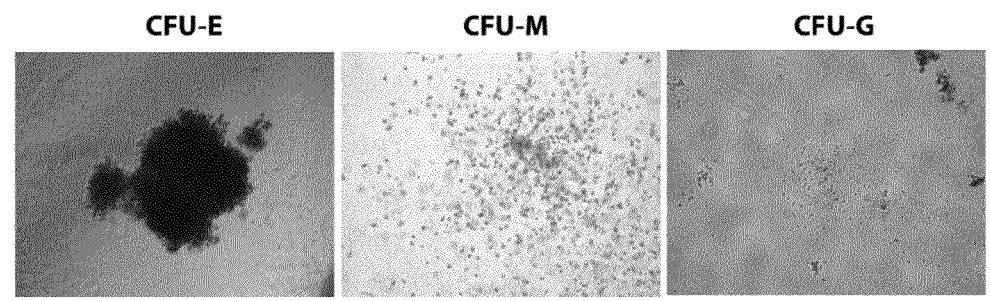
Figure 11:
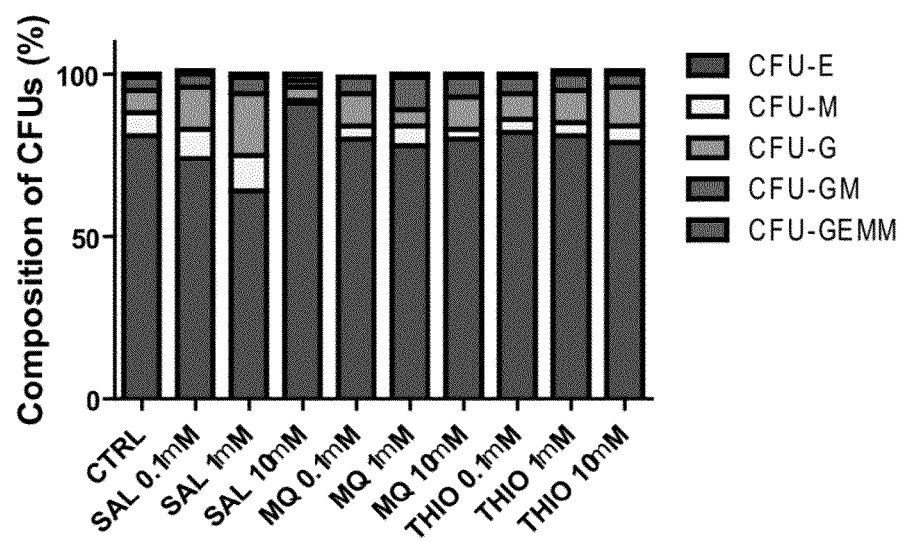

Thioridazine Selectively Induces Neoplastic hPSC Differentiation and Reduces Human AML Blasts without Affecting Normal Hematopoietic Stem/Progenitor Cells The responses to thioridazine and mefloquine were evaluated in both normal (FIG. 10a) and neoplastic hPSCs (FIG. 10b) at three concentrations using quantitative flow cytometry to detect the loss of Oct4 and reveal the degree of differentiation. Salinomycin, a reported selective inhibitor of breast CSCs (Gupta et al., 2009), was included for comparison. At 10 µM, all compounds reduced the number of cells, but the levels of Oct4 in remaining normal hPSCs was not below levels observed with BMP4 treatment (FIG. 10a). This same response was replicated in fibroblast-derived human iPS cells, (FIG. 11a), representing an additional normal hPSC line from a distinct (adult) origin, indicating the effects are not specific to embryonic sources. When the same compounds were used to treat neoplastic hPSCs, mefloquine and thioridazine treatments caused reductions in cell number and the levels of Oct4 in neoplastic hPSCs. Only thioridazine was able to reduce levels of Oct4 below BMP4 differentiation controls (FIG. 10b), indicating the ability of thioridazine to overcome neoplastic hPSC differentiation block. A more comprehensive dose response of all compounds was performed on neoplastic hPSCs to confirm this response (FIG. 11b). To identify compounds that selectively differentiate neoplastic hPSCs quantitatively, the ratio of normalized percentage of Oct4+ cells between normal and neoplastic hPSCs in response to these compounds was determined. For example, a ratio of 1 suggests equivalent differentiation whereas a ratio >1 defines relatively more differentiation in neoplastic hPSCs vs. normal hPSCs. Only thioridazine, at both 1 µM and 10 µM, had a significant impact on inducing differentiation of neoplastic hPSCs over normal hPSCs (FIG. 10c). Rapid accumulation of the cell stress marker p53 (FIG. 10d) and its transcriptional target p21 (FIG. 10e) were used to further distinguish differentiation induction from cellular toxicity. Treatment of neoplastic hPSCs with the toxic chemotherapeutic agent etoposide resulted in high levels of p53 and p21 after 24 h. However, treatment with 10 µM thioridazine or BMP4, unlike agents that induce toxicity alone, resulted in no accumulation of p53 or p21, consistent with induced differentiation rather than stress-response programs. Furthermore, thioridazine treatment led to expression of differentiation genes quantified by TaqMan Low-Density Array-qPCR in neoplastic hPSCs. An upregulation in 21 of 50 differentiation-associated genes (FIG. 10f) was observed in treated neoplastic hPSCs consistent with differentiation-inducing effects of thioridazine.

To examine the potential similarities in chemical response of neoplastic hPSCs to somatic CSCs, normal and neoplastic populations of the human hematopoietic system were assessed. Experimentally, self-renewal and differentiation of both human hematopoietic stem-progenitor cells (HSPCs) and Leukemic Stem Cells (LSCS) can be interrogated by powerful and well established in vitro and in vivo assays uniquely available to the hematopoietic system, making it an ideal tissue to evaluate the potential surrogacy of using normal and neoplastic hPSCs as a primary screening tool for anti-CSC compounds. Lineage-depleted umbilical cord blood (CB lin−) is highly enriched for HSPCs and is a reliable source of normal somatic SCs capable of self-renewal and multilineage differentiation to all blood lineages. Acute myeloid leukemia (AML) is a hematological neoplasia characterized by a block in mature myeloid differentiation that is sustained by a self-renewing LSC (Bonnet and Dick, 1997; Lapidot et al., 1994).

As such, progenitor assays in methylcellulose were conducted with HSPCs and 5 AML patient samples; each treated with thioridazine, mefloquine, or salinomycin in order to assess each compound's impact on in vitro clonogenic and multilineage hematopoietic differentiation. Representative cell pellets of the total colony-forming units (CFUs) generated from HSPCs (FIG. 10g) and AML (FIG. 10h) treated with each compound are shown. Thioridazine treatment resulted in a reduction in AML proliferation/clonogenic capacity while retaining HSPC multilineage differentiation (FIG. 11c). Changes in multilineage differentiation were quantified based on the enumeration of CFUs generated following treatment of HSPCs (FIG. 10i) and AML patient (FIG. 10j) samples with these compounds. At both 1 µM and 10 µM salinomycin reduced AML-blast CFU potential (FIG. 10j), but also reduced HSPC CFU potential over all doses tested (FIG. 10i) indicative of non-specific toxicity in the hematopoietic system. In contrast, mefloquine and thioridazine reduced AML-blast CFU formation (FIG. 10j) while having little effect on HSPC CFU potential (FIG. 10i) and multilineage composition (FIG. 11d) indicating that mefloquine and thioridazine do not alter normal hematopoiesis.

The most desired outcome of compounds identified toward clinical use would entail preferential elimination of AML-blast CFU generation while preserving normal HSPC progenitor capacity. The ratio between total CFUs generated from HSPC vs. AML-blasts to reveal the highest selectivity for targeting AML was calculated (FIG. 10k). A ratio of 1 suggests equivalent normal to neoplastic progenitor potential whereas a ratio >1 defines a compound that selectively reduces AML-blast CFU potential. Salinomycin (1 µM), mefloquine (10 µM), and thioridazine (10 µM) doses yielded the highest ratio values for each compound (FIG. 10k) and were thus selected for in vivo evaluation. Thioridazine 10 µM, in particular, demonstrated the highest ratio of all compounds, but most importantly was the only compound to show a significantly lower AML-blast CFU potential relative to normal HSPC CFU potential (FIG. 10k). To address whether thioridazine's specificity for reducing the clonogenic potential of AML-blast CFUs was due to induction of differentiation, the frequency of CD11b, a marker of granulocytic maturation, in patient AML cells was assayed in response to thioridazine treatment (FIG. 10l). A marked increase in the frequency of granulocytic AML-blast cells was observed with treatment duration (FIG. 10l) indicating that thioridazine exhibits its specific targeting of AML cells through induction of differentiation. This finding is analogous to differentiation-induction demonstrated in neoplastic hPSCs (FIG. 10a-f) and confirms the robust readout of this screening platform towards identifying agents able to differentiate neoplastic cells. This result also suggests that thioridazine may represent the best candidate for specific targeting of AML CSCs that requires testing using in vivo human-mouse xenograft assays.

Example 10

Thioridazine Reduces LSC Function while Sparing Normal HSPCs

Figure 12:
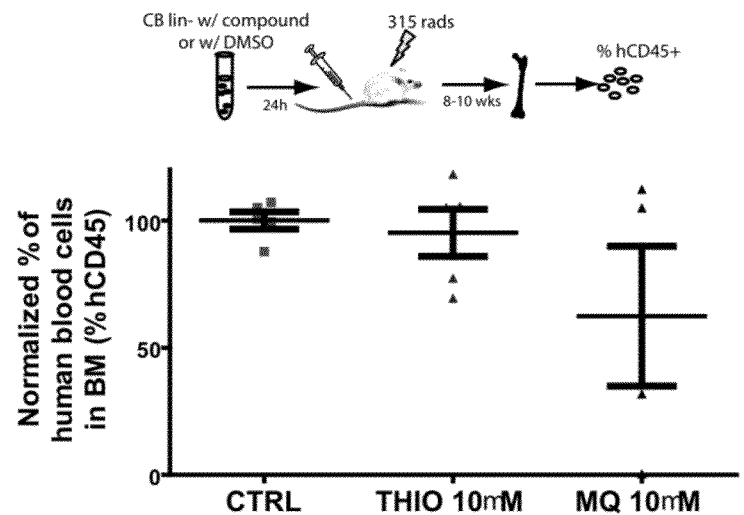
FIG. 12 shows thioridazine's effect on HSC and LSC engraftment. (A) Frequency of human CD45+ cells in the bone marrow following HSPC treatment with thioridazine 10 μM (THIO 10 μM) or mefloquine 10 μM (MQ 10 μM). Values normalized to DMSO-treated HSPC control (CTRL) samples. Total of two HSPC samples evaluated. Mean+/−SEM. (B) Representative flow cytometry plots of side scatter (SSC) versus myeloid (CD33) or lymphoid (CD19) markers within the hCD45+ population. 12(C) Frequency of CD45+ CD33+ AML blast cells in the bone marrow (BM) following treatment of AML with thioridazine 10 μM (THIO 10 μM) or mefloquine 10 μM (MQ 10 μM). Values normalized to DMSO-treated AML control (CTRL) samples. Total of two AML patient samples evaluated. (D) Representative flow plots of CD33 vs CD45 in DMSO-treated control (CTRL) populations versus thioridazine treated (THIO 10 μM). (E) Ratio of normalized percent hCD45 HSPC engraftment per normalized percent CD45 CD33 AML blast engraftment. (*) p<0.05
Figure 12:
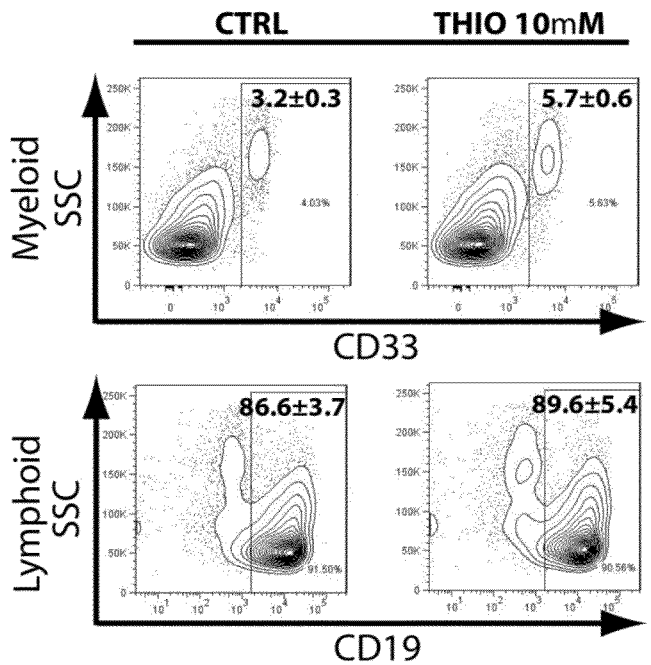
Figure 12:
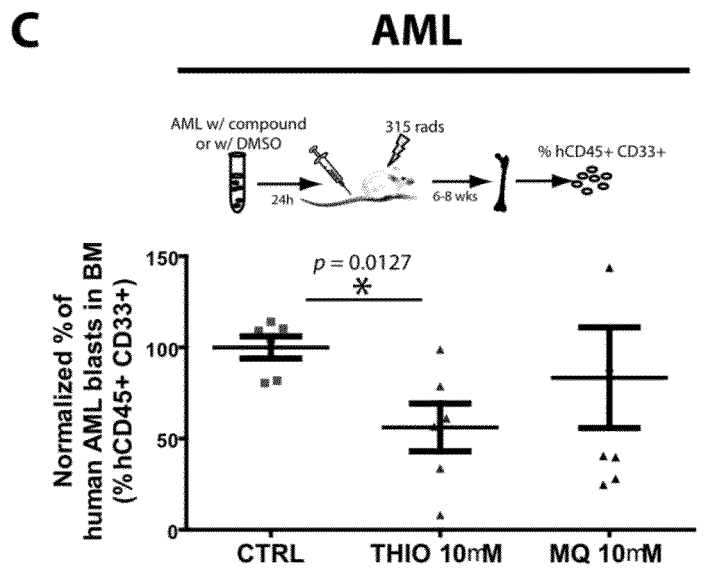
Figure 12:
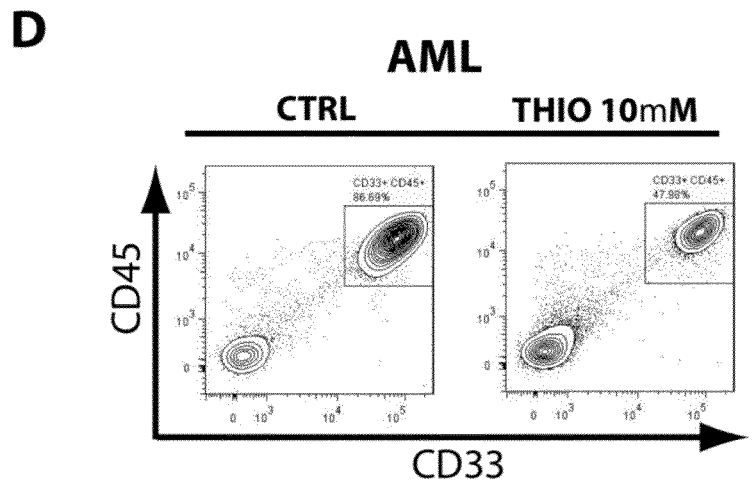
Figure 12:
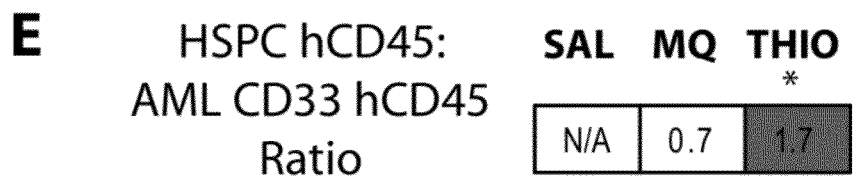

To delineate whether the inhibition of AML-blasts detected in vitro was due to the compounds affecting the neoplastic stem cell compartment, xenotransplantation studies (Dick, 2008) that functionally define LSCs and hematopoietic stem cells (HSCs) were conducted (FIG. 12). Treatment of HSPCs with salinomycin (1 µM) significantly reduced hematopoietic engraftment to almost non-detectable levels (FIG. 13a) revealing that this compound interferes with normal hematopoiesis from HSPCs and was thus excluded from further evaluation as it is unlikely to provide the selective anti-CSC therapeutic targeting desired. In contrast, mefloquine (10 µM) treatment displayed a slight, yet insignificant, reduction in HSC capacity relative to controls (FIG. 12a). However, mefloquine proved ineffective in reducing AML LSC capacity and was thus discontinued from further evaluation due to absence of selective effects (FIG. 12c).

Figure 13:
FIG. 13 shows in vivo response to drug treatment. (A) The normalized frequency of human CD45+ cells in the bone marrow following HSPC treatment with salinomycin 1 μM (SAL 1 μM) relative to DMSO-treated (CTRL) samples. Total of two HSPC samples evaluated. Mean+/−SEM. (****) p<0.0001 (B) Thioridazine's effect on HSC and LSC splenic engraftment. (B, top) Frequency of human CD45+ cells in the spleen following HSPC treatment with thioridazine 10 μM (THIO 10 μM). Values normalized to DMSO-treated HSPC control (CTRL) samples. Total of two HSPC samples evaluated. Mean+/−SEM. (B, bottom) CD45+ CD33+ blast cells in the spleen following thioridazine 10 μM (THIO 10 μM) treatment of AML. Values normalized to DMSO-treated AML control (CTRL) samples. Total of two AML patient samples evaluated. (C) Thioridazine's effect on erythrocytic and megakaryocytic regeneration. Composition of human blood cells detected in the xenotransplant BM injected with HSPC treated with thioridazine 10 μM (THIO 10 μM) or with DMSO (CTRL). Red blood cells (RBC) are defined by glycophorin A positivity and platelets by CD41a. (D) Confirmation of myeloid leukemic engraftment of xenotransplants with AML. Flow cytometry of side scatter versus CD19, a marker of lymphoid cells. Inset number represents mean+/−SEM. (E-F) Thioridazine's effect on HSC and LSC in vivo self-renewal. Engraftment levels of (E) hCD45+ cells or (F) hCD45+CD33+ in BM of secondary xenotransplants receiving equal number of hCD45 cells explanted from (E) primary CBlin− or (F) primary AML transplants treated with thioridazine (THIO 10 μM) or DMSO control (CTRL). Each bar n=3 mice, mean+/−SEM.
Figure 13:
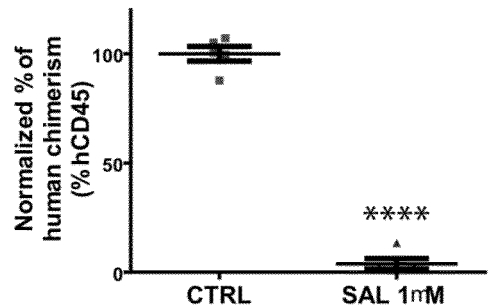
Figure 13:
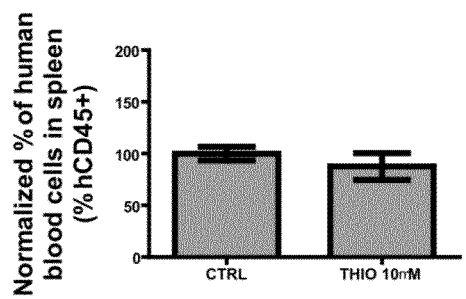
Figure 13:
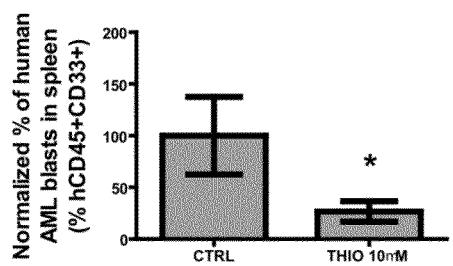
Figure 13:
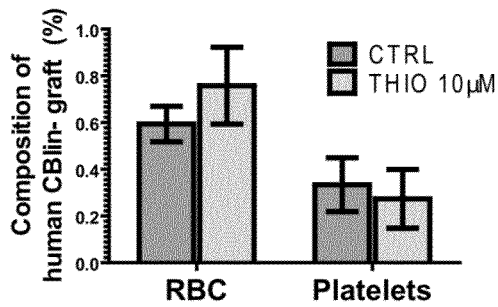
Figure 13:
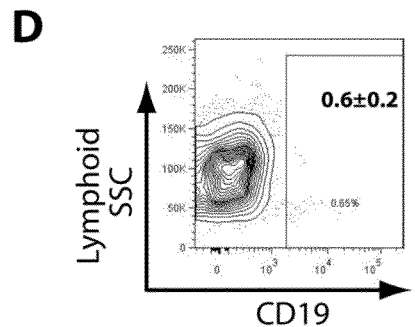
Figure 13:
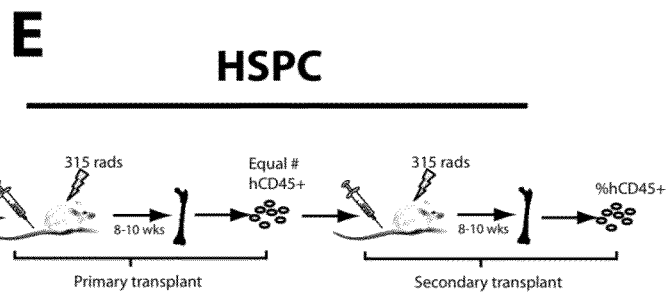
Figure 13:
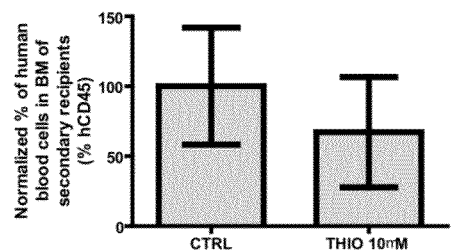
Figure 13:
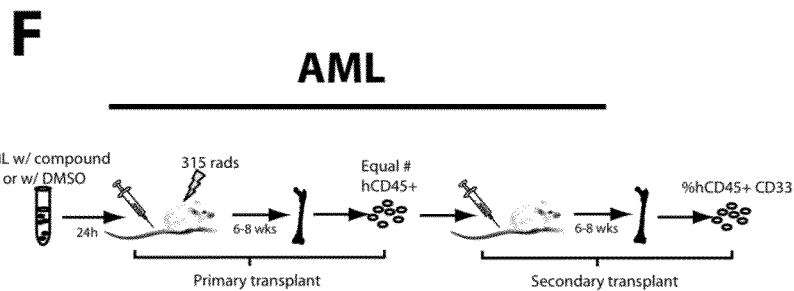
Figure 13:
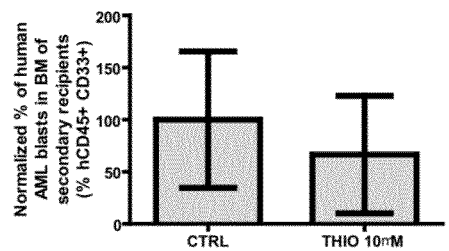

In contrast to both salinomycin and mefloquine, treatment of HSPCs with thioridazine 10 µM displayed the same level of bone marrow (BM) engraftment (FIG. 12a) and splenic engraftment (FIG. 13b) as control vehicle treated cells. Multilineage reconstitution capacity was identical from control- and thioridazine-treated human HSCs with myeloid (FIG. 12b), lymphoid (FIG. 12b), erythroid (FIG. 13d), and megakaryocytic development (FIG. 13d) completely unaffected. As measured by secondary serial transplantation, thioridazine treatment did not affect HSC self-renewal as compared to control-treated samples (FIG. 13f). However, in sharp contrast to salinomycin and mefloquine, thioridazine treatment was able to significantly reduce leukemic disease-initiating AML LSCs (FIGS. 12c-d; FIG. 13c; FIG. 13e). Calculating the ratio of HSPC normal hemaotopoietic regeneration (% hCD45+) to AML leukemogenesis (% CD33+ hCD45+ blasts) revealed that thioridazine significantly reduced LSC function while preserving normal HSC capacity (FIG. 12e). In the absence of thioridazine, no difference in the level of leukemic engraftment of secondary transplant recipients was observed. This suggests that continued exposure to this drug is necessary to inhibit leukemogenesis in secondary recipients. These data demonstrate that thioridazine selectively targets somatic CSCs whilst having no effect on normal SC properties in vivo. As thioridazine was identified through the use of a novel differential screening platform using normal and neoplastic hPSCs in vitro, the functional effects of thioridazine provide an example of the predictive value of using human PSCs to understand somatic CSCs.

Example 11

Dopamine Receptors Demarcate Human CSCs

Figure 14:
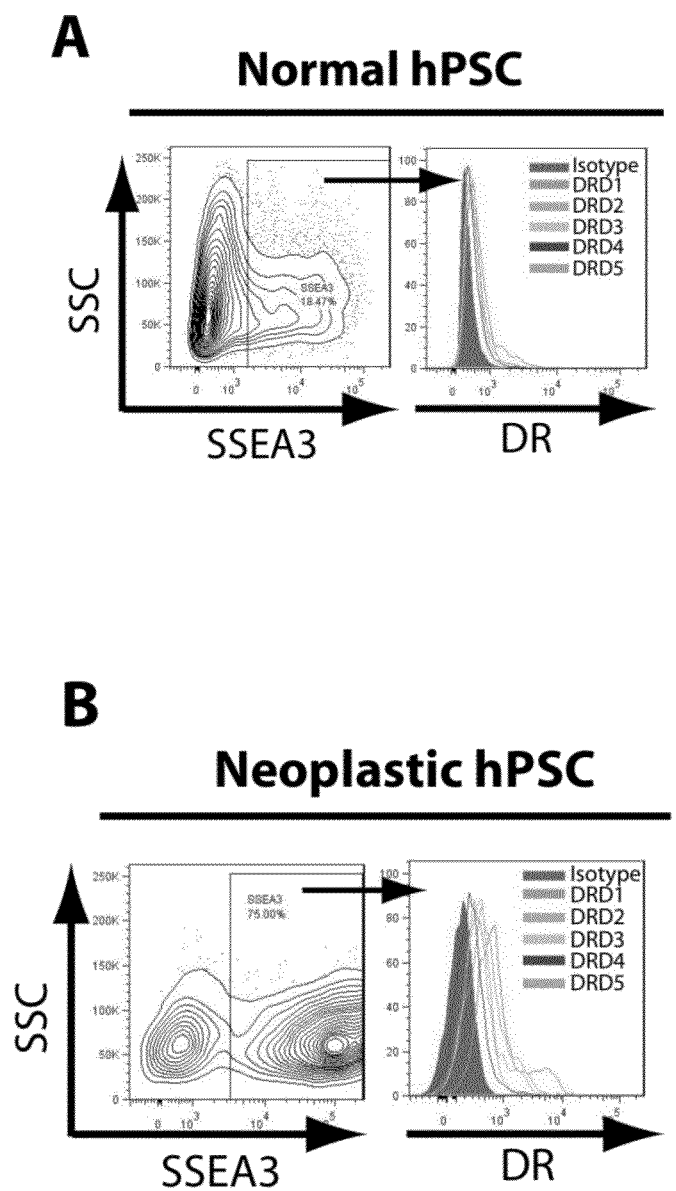
FIG. 14 shows dopamine receptors expressed on neoplastic stem cells. (A-B) Flow cytometry of (A) normal H9 and (B) neoplastic v1H9-Oct4-GFP cells stained with SSEA3 and all five dopamine receptor (DR) subtypes. DR expression in the SSEA3+ fraction is shown. (C) Flow cytometry of lineage-depleted cord blood (HSPC) stained with CD34, CD38 and all five DR subtypes. DR expression is presented in the gated populations. (D) Flow cytometry of 13 AML patient samples stained for all five DRs along with associated FAB classification. (E-F) Frequency of AML blast cells (CD33+CD45+) from patient samples which are also positive for (E) DRD3 and (F) DRD5. A total of 8 AML patient samples were assessed for leukemic-initiation potential in xenotransplantation recipients. Leukemic-initiating was defined as human engraftment >0.1% of CD33+ hCD45+ in mouse bone marrow. Four leukemic-initiating AML samples were assayed in 22 mice while 4 non-initiating AML samples were assayed in 17 mice. Total n=8 AML samples, mean+/−SEM.
Figure 14:
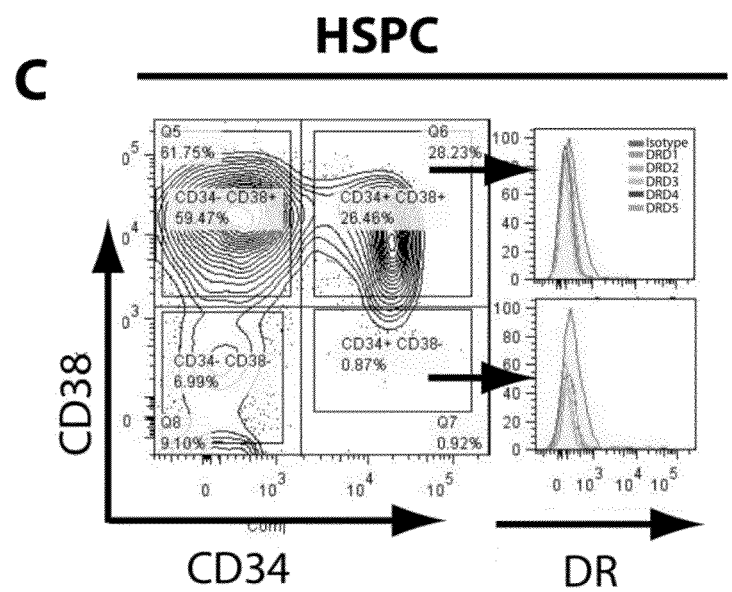
Figure 14:
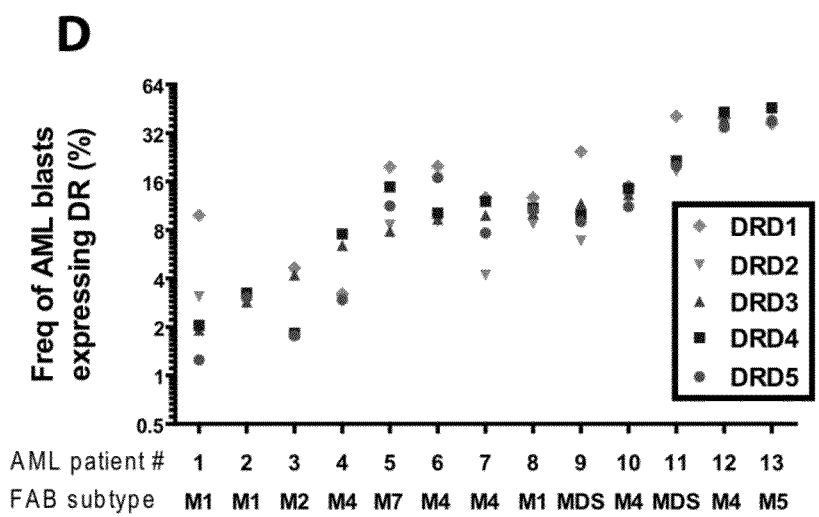
Figure 14:
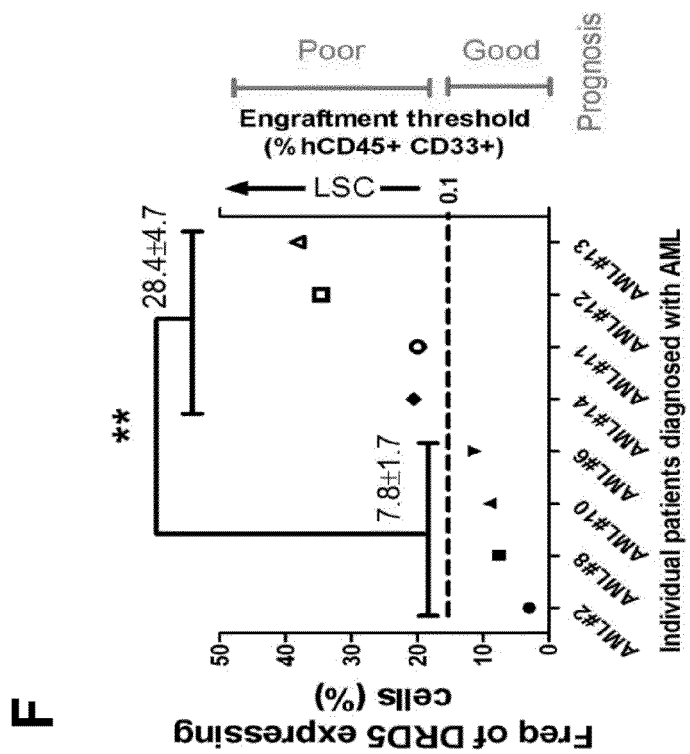
Figure 14:
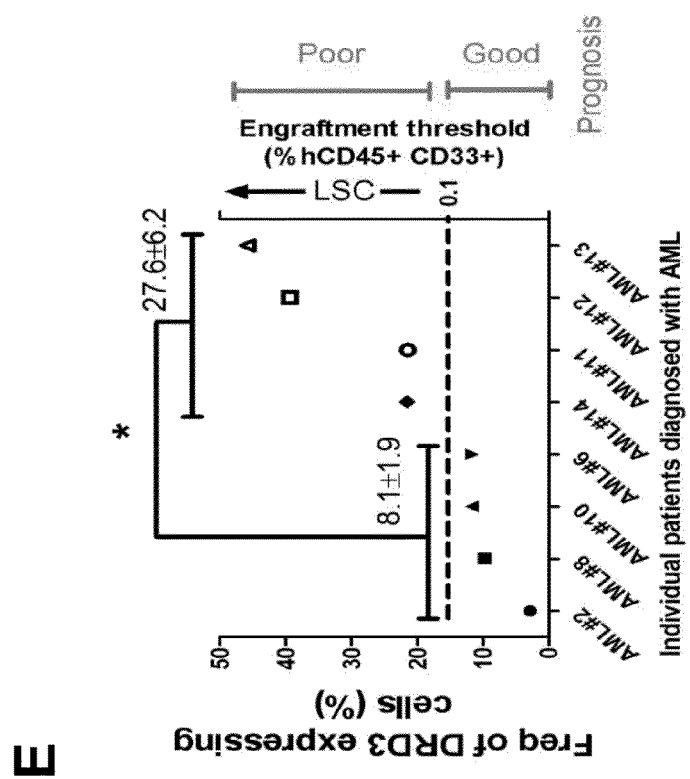
Figure 15:
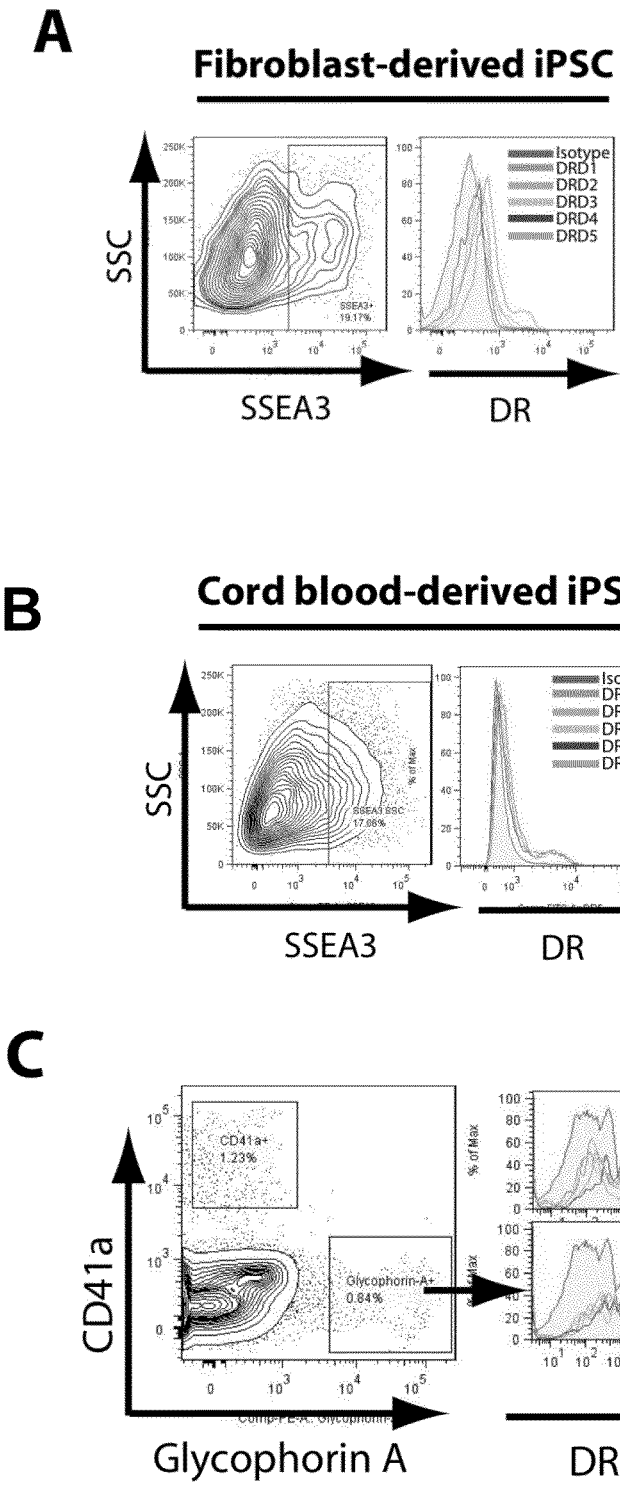
FIG. 15 (A-B) Flow cytometry SSEA3+ fraction in (A) fibroblast-derived hiPSC and (B) umbilical cord blood-derived hiPSC stained for all five dopamine receptors. (C) Dopamine receptors expression of human blood populations. Flow cytometry of cord blood mononuclear cells stained for (C) erythroid (glycophorin A), (C) megakaryocytes (CD41a); (D) T-cells (CD3), (D) B-cells (CD19); (E) monocytes (CD14) and (E) granulocytes (CD15). Staining for all five DRs in the gated populations are shown as histograms. (F) Summary of DR localization in the blood populations. (G) Flow cytometry of AML patient showing DR in gated populations.
Figure 15:
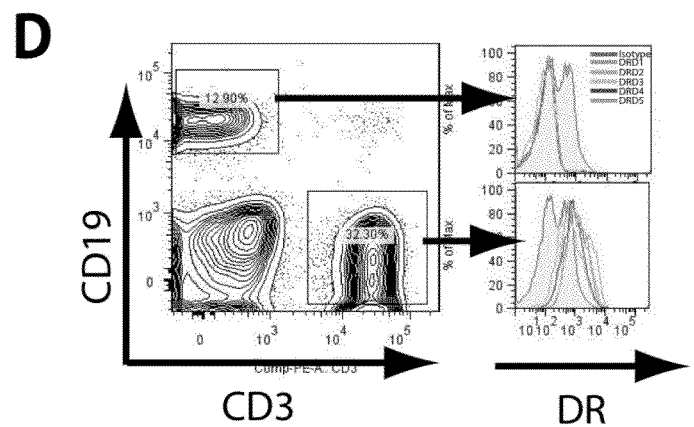
Figure 15:
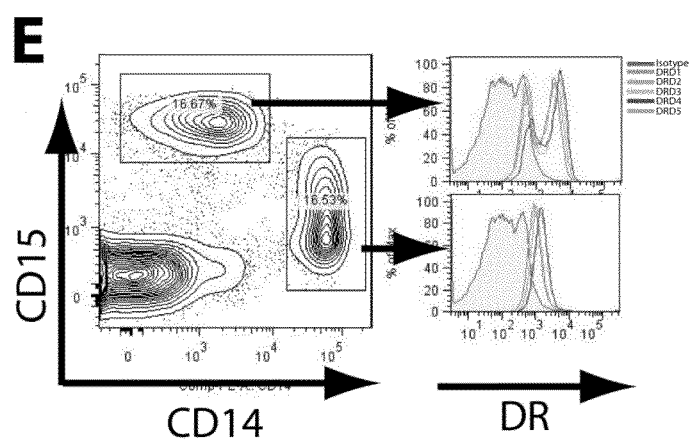
Figure 15:
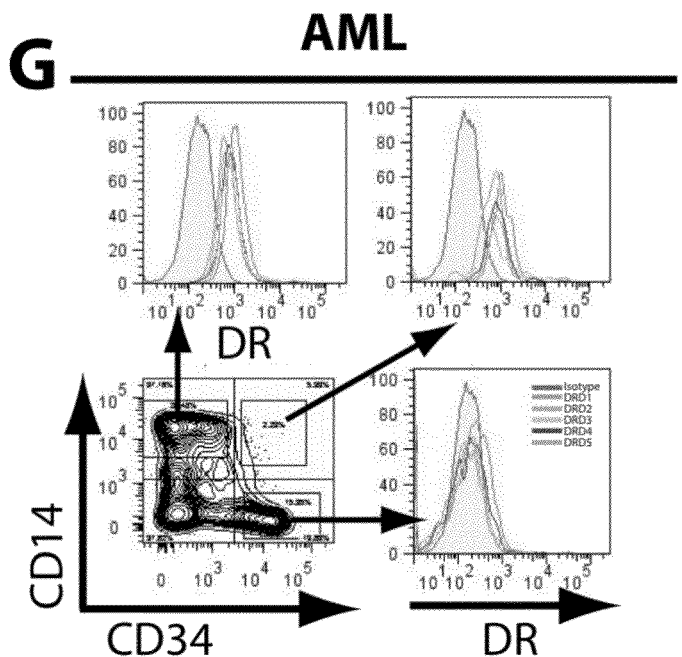

Thioridazine is known to act through the dopamine receptors (DR 1-5) (Beaulieu and Gainetdinov, 2011; Seeman and Lee, 1975). To assess whether the mechanism of thioridazine action to selectively interfere with human CSCs vs. normal SCs is via DR antagonism, DR cell surface expression was analyzed. To date, five DRs have been identified and divided into $D_1$-family (D1 and D5) and $D_2$-family (D2, D3, and D4) receptors (Sibley and Monsma, 1992). Normal hPSCs expressing the pluripotent marker SSEA3 were devoid of DR expression (FIG. 14a and FIG. 15a-b). In contrast, neoplastic hPSCs expressed all five DRs (FIG. 14b). The observed differential expression of DRs and the selective inhibition of thioridazine for neoplastic hPSCs suggest that inhibition of DR signaling may play a role in selective targeting of human CSCs vs. normal SCs.

To expand the potential role of DRs in CSCs based on the functional role of thioridazine treatment we examined whether DR antagonism could account for the loss of LSC function following thioridazine treatment. Expression of DR1-5 was analyzed in HSPCs (FIG. 14c) and human hematopoietic mononuclear cells from normal CB (FIGS. 15c-f) and AML patient samples (FIG. 14d and FIG. 15g). DRs were not observed in the primitive HSCs or progenitor populations of CB (identified as the CD34+38− or CD34+ 38+ fractions, respectively (Bhatia et al., 1997)) (FIG. 14c) indicating that HSCs and progenitors do not express the targets for thioridazine. Similarly, DRs were undetectable on the surface of erythroid (FIG. 15c), megakaryocytic (FIG. 15c), and lymphoid cells (FIG. 15d). Only monocytes defined as CD14+ and approximately half the population of granulocytes defined as CD15+ expressed DRs (FIGS. 15e-f). All of the 13 AML patient samples analyzed contained a population of DR+ blasts with varying levels of all five receptors (FIG. 14d) and were predominately detected in CD34+/CD14+ cells (FIG. 15g). However, unlike normal HSCs, CD34+ cells do not correlate with LSC capacity in human AML (Taussig et al., 2008) and have recently been identified in numerous subfractions devoid of CD34 or CD38 (Eppert et al., 2011). Observations of differential DR expression in normal and AML human hematopoietic samples strongly suggest the human AML LSCs are heterogeneous and drug targeting should be based on molecular pathways instead of surrogate phenotype predications.

Whether the DR expression in AML-blasts was correlative to incidence of LSCs in AML patients was investigated. AML samples with a large fraction of DRD3+ blasts (FIG. 14e) and DRD5+ blasts (FIG. 14f) contain LSCs as they are able to initiate leukemia in xenotransplantation recipients, unlike AML patient samples with significantly lower levels of DRs that do not contain LSCs. Samples from AML patients containing LSCs have been correlated to poor prognostic outcome while non-LSC samples demonstrate a good prognosis (Eppert et al., 2011). High levels of DR expression correlate with poor prognosis while low levels demonstrate good prognosis (FIG. 14e-f) suggesting that DR assessment has prognostic biomarker applications and is less complex than molecular signatures or LSC readouts for each AML patient.

Example 12

Thioridazine Antagonism of DR Inhibits Human AML

To better understand the functional role of DR in human AML, two AML cell lines derived from patients; AML-OCI2 and AML-OCI3, were utilized (Koistinen et al., 2001).

Figure 16:
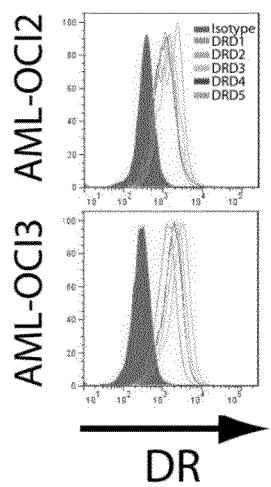
FIG. 16 shows that thioridazine inhibits dopamine receptor signaling in AML and that combined treatment with cytarabine has a synergistic effect on cancer cells. (A) DR expression of AML-OCI2 and AML-OCI3 cell lines. (B) Cell counts of AML-OCI2 and AML-OCI3 cells treated with three DR antagonist drugs. Values are normalized to DMSO-treated control samples. Each bar n=3; mean+/−SD. (C-D) Viable cell counts (7AAD−, Hoechst+) of same cell lines treated with (C) 7OH-DPAT, a DR D2-family agonist, or (D) SKF38393, a DR D1-family agonist, in serum-free conditions. Values are normalized to DMSO-treated control samples. Each bar n=3; mean+/−SD. (E-F) Single versus combined drug treatment of AML and HSPC. (E) Single drug treatment of patient AML and HSPC with thioridazine (Thio 10 μM) or cytarabine (AraC) followed by CFU generation and enumeration. (F) Combined thioridazine and AraC treatment of the same patient samples and CFU generation and enumeration. The normalized ratio of HSPC:AML CFUs is calculated for each concentration and displayed above the appropriate bar pairs. The effective concentration for AraC treatment ($Ec_{AraC}$) is reduced from 100 nM to 1 nM with the combination of thioridazine ($Ec_{AraC+Thio}$). Alternatively, 100 nM AraC combined with thioridazine exhibits almost complete elimination of blast-CFUs while preserving HSPC function. HSPC bar n=4, two CBlin− samples; AML bars n=4 AML patient samples, mean+/−SEM. (*) p<0.05, () p<0.01, (*) p<0.001, (****) p<0.0001.
Figure 16:
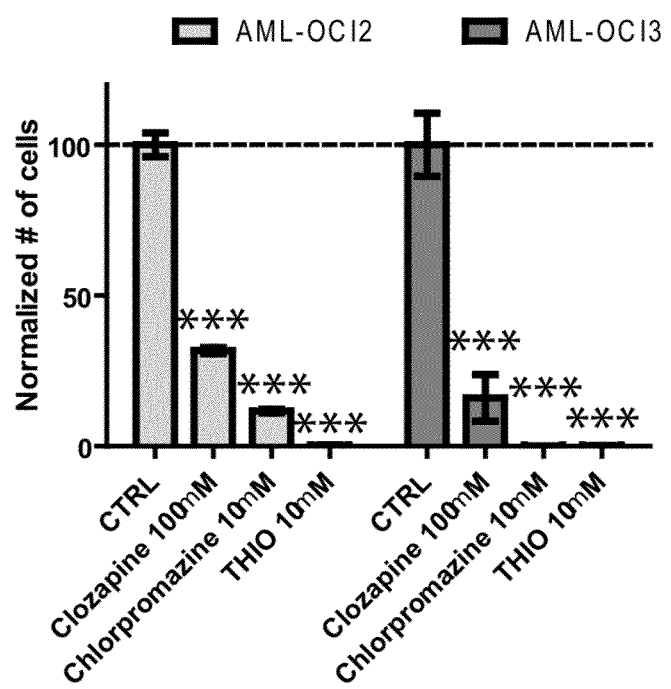
Figure 16:
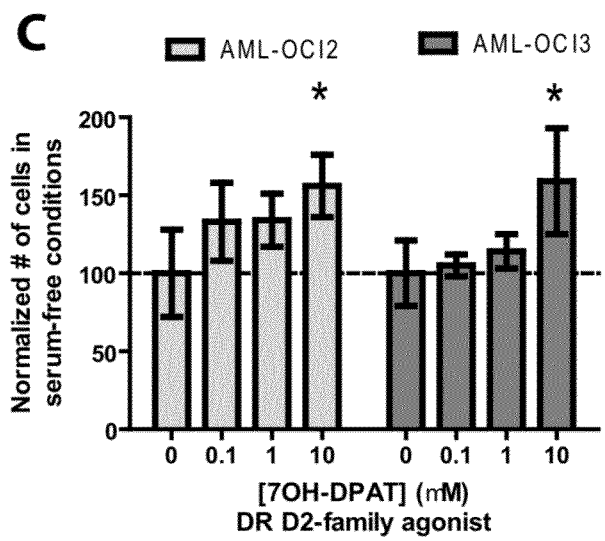
Figure 16:
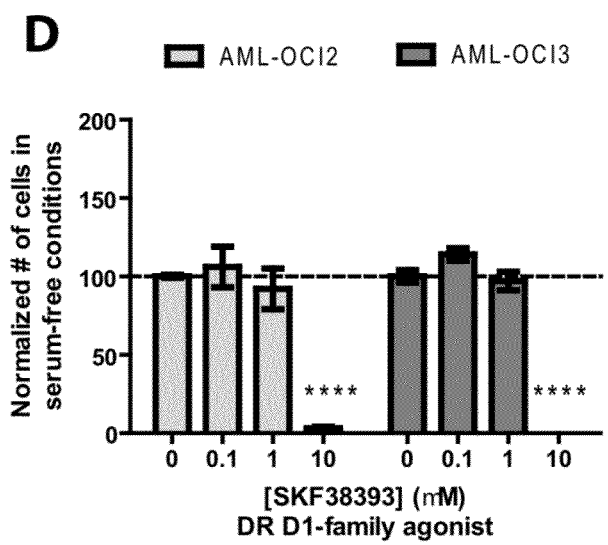
Figure 16:
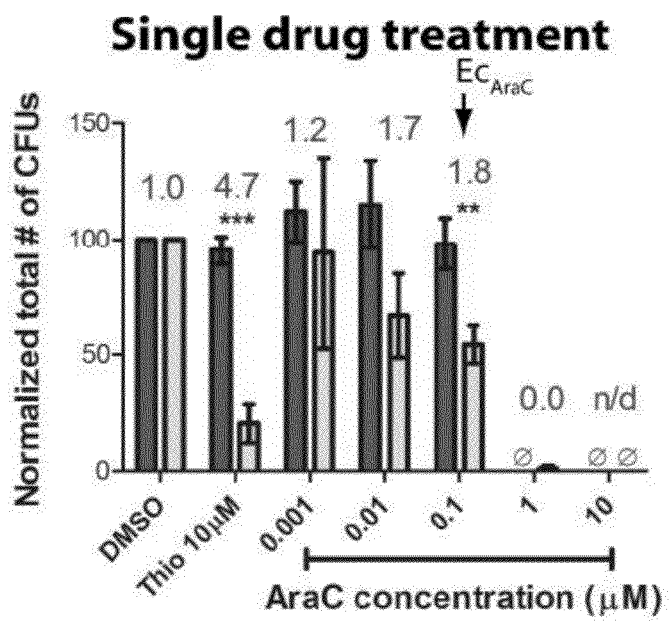
Figure 16:
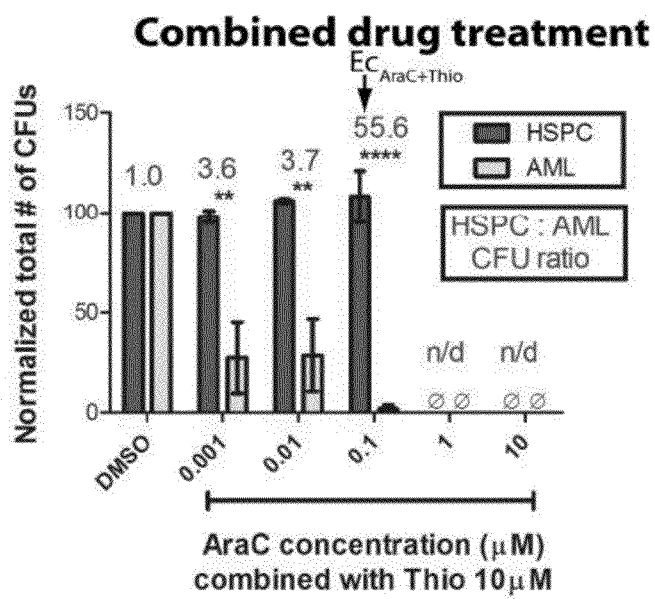

Like primary samples, these two cell lines revealed expression for each DR1-5 (FIG. 16a) at markedly higher levels than seen in patient samples. Due to the bioavailability of dopamine in fetal bovine serum (FBS) (Little et al., 2002), serum-free conditions were employed to assess the role of DRs in AML. Both AML lines were treated with thioridazine and compared to other known DR antagonists clozapine and chlorpromazine (Seeman and Lee, 1975). All three DR antagonists reduced the number of AML cells upon treatment (FIG. 16b). To further evaluate the specificity of DR targeting on human AML cells, patient AML samples were divided into DR+ and DR− subfractions using fluorescence activated cell sorting before being treated with DMSO vehicle or thioridazine for 24 h and then assayed for blast-CFU content. A reduction in blast-CFU generation was only observed in the DR+ subfraction treated with thioridazine (FIG. 17a) whereas no reduction was observed in DR− subfraction treated with thioridazine (FIG. 17b). Conversely, the addition of a DR D2-family agonist, 7OH-DPAT, increased the number of AML cells (FIG. 16c). DR D2-family and D1-family exert opposing actions on intracellular signaling leading to differential biological effects (Self et al., 1996). Treatment with a DR D1-family agonist, SKF38393, resulted in a significant reduction in AML cell number confirming that D2-family signaling is necessary for AML cell survival (FIG. 16d). These combined results suggest the mechanism of thioridazine's action is through antagonism of D2-family DRs and not due to off-target effects, and identifies a novel avenue of CSC targeting via DR signaling.

Example 13

Combination Therapy Using a DR Antagonist and a DNA Synthesis Inhibitor

Upon establishing thioridazine's anti-LSC effect at clinically-tolerable doses (FIG. 17c) it was investigated whether this drug could be combined with conventional AML chemotherapy using the DNA synthesis inhibitor cytarabine (AraC). Although AraC is the gold-standard chemotherapeutic used in both induction and consolidation therapy of adult human AML, this treatment poses significant morbidity and mortality risks at high doses (Estey and Dohner, 2006). Using normal HSPC vs. AML-blast detection, at concentrations >1 µM AraC induced complete toxicity of AML CFU blasts, however, was equally sufficient at eliminating normal HSPCs (FIG. 16e). Using various doses we identified AraC's effective concentration ($EC_{AraC}$), as defined by the concentration that reduced AML-blast-CFU while retaining HSPC function, to be at 100 nM (FIG. 16e). However, the combination of thioridazine at 10 µM with AraC reduced the effective concentration ($EC_{AraC+Thio}$) to 1 nM (FIG. 16f) representing a 100-fold reduction in AraC dosage required. This combined effect of thioridazine is likely to have significant benefit to AML patients as it can reduce the severe cytotoxic effects associated with high dose AraC therapy, as illustrated in FIG. 17d.

Alternatively, the combination of thioridazine at 10 µM with AraC 100 nM demonstrates almost complete elimination of AML-blast-CFUs while preserving HSPC function (FIG. 16f) suggesting that these specified concentrations can induce remission and prevent relapse of AML in patients. Collectively, these data show the synergistic benefit of combining an anti-LSC agent (thioridazine) with an anti-proliferative agent (AraC) currently used as a single first line treatment for human AML towards targeting CSCs, in addition to other cells in the leukemogenic hierarchy.

Example 14

Combination Therapy Using DR Antibodies

AML cells are treated with primary antibodies which bind to one of the DRs (DR1, DR2, DR3, DR4 and DR5) and then with a secondary antibody (which specifically recognizes and binds to the primary antibody) conjugated to a cytotoxic agent. The serial binding of primary and then secondary antibodies permits the specific targeting of cells expressing DR and delivery of the cytotoxic payload. Numerous cytotoxic agents can be chemically grafted to the secondary antibody.

The Ribosome-inactivating protein, saporin, is conjugated to a secondary antibody and can enter the cells upon receptor internalization thereby breaking away and inactivating the cell's ribosomes leading to protein inhibition and ultimately cell death. These sequentially administered antibodies are analogous to thioridazine and AraC combination therapy in that the primary antibody binds to DR (a thioridazine-like response) while the secondary antibody delivers the saporin cytotoxic effect (an AraC-like response). This antibody system can optionally be designed into a single DR antibody conjugated to cytotoxic agent.

Following treatment of AML cells with this primary and secondary antibody combination for a defined period (24 h), the AML cells are plated in methylcellulose conditions to generate blast-CFUs and scored relative to AML cells treated with secondary antibody only (i.e. without primary DR antibodies). Cells treated with primary DR antibodies and secondary saporin-conjugated antibodies are observed to significantly reduce AML blast-CFU generation relative to the control cells treated with secondary antibody.

Example 15

Combination Treatment of Leukemic Cell Lines with Cytarabine and Thioridazine

OCI-AML2 and OCI-AML3 are AML patient derived cell lines that were plated in flat-bottom 96 well plates at 25,000 cells per well in 100 µl of culture medium. Cells were treated with various concentrations of cytarabine (AraC) ranging from 0.01-1 µM in standard culture medium as single treatment or in combination with thioridazine 10 µM for 24 h. The cells were then stained with the fluorescence viability stain 7-Aminoactinomycin D (7AAD) and measured using a flow cytometer with high throughput screening (HTS) adapter operated in a volumetric cell counting mode. The live cells were defined by the events within gates establish forward and side-scatter profile in addition to being negative for 7AAD staining.

Figure 19:
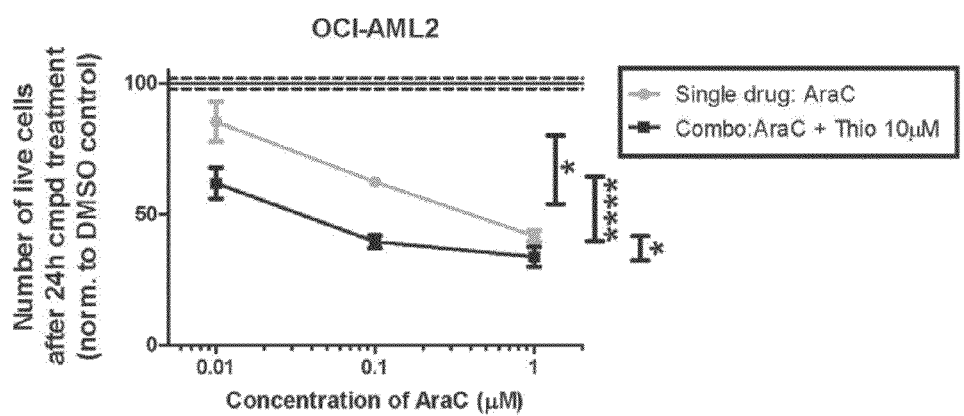
FIG. 19 shows dose-response curves for the number of live cells in (A) OCI-AML2 and (B) OCI-AML3 cell lines treated at various concentrations of cytarabine (AraC) as a single treatment (Single drug: AraC) or in combination with thioridazine 10 µM (Combo: AraC+Thio 10 µM) normalized to DMSO control (shown as a solid line intersecting 100 on the y-axis with dashed lines representing the standard deviation of the control).
Figure 19:
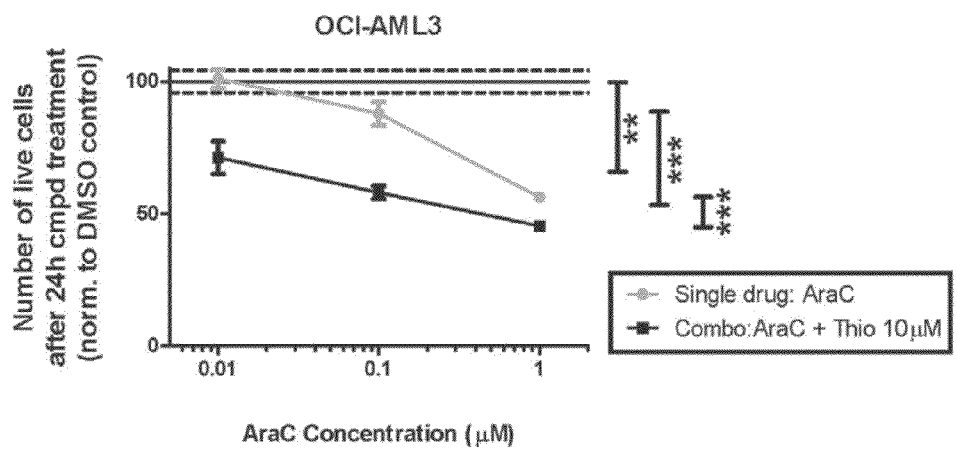

As shown in FIG. 19, treatment with a combination of cytarabine and thioridazine is highly effective at reducing the viability or proliferation of the leukemic cell lines. At every dose of AraC tested, the combination with thioridazine significantly reduced the number leukemic cells relative to treatment with AraC alone, demonstrating that the combination of AraC+Thio 10 uM is more effective in reducing leukemic cell viability than AraC itself. Furthermore, for each dose of AraC tested, the same reduction in the level of leukemic cells can achieved by using approximately 10-fold less AraC in combination with thioridazine. This 10-fold increase in AraC's effectiveness represents a clinical benefit to patients undergoing AraC chemotherapy and, for example, suggests that the treatment regime can be prolonged with lower doses of AraC when used in combination with thioridazine.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Adewumi, O., Aflatoonian, B., Ahrlund-Richter, L., Amit, M., Andrews, P. W., Beighton, G., Bello, P. A., Benvenisty, N., Berry, L. S., Bevan, S., et al. (2007). Characterization of human embryonic stem cell lines by the International Stem Cell Initiative. Nat Biotechnol 25, 803-816.

Beaulieu, J. M., and Gainetdinov, R. R. (2011). The physiology, signaling, and pharmacology of dopamine receptors. Pharmacol Rev 63, 182-217.

Ben-Porath, I., Thomson, M. W., Carey, V. J., Ge, R., Bell, G. W., Regev, A., and Weinberg, R. A. (2008). An embryonic stem cell-like gene expression signature in poorly differentiated aggressive human tumors. Nat Genet 40, 499-507.

Bhatia, M., Wang, J. C., Kapp, U., Bonnet, D., and Dick, J. E. (1997). Purification of primitive human hematopoietic cells capable of repopulating immune-deficient mice. Proc Natl Acad Sci USA 94, 5320-5325.

Bonnet, D., and Dick, J. E. (1997). Human acute myeloid leukemia is organized as a hierarchy that originates from a primitive hematopoietic cell. Nat Med 3, 730-737.

Boyer, L. A., Lee, T. I., Cole, M. F., Johnstone, S. E., Levine, S. S., Zucker, J. P., Guenther, M. G., Kumar, R. M., Murray, H. L., Jenner, R. G., et al. (2005). Core transcriptional regulatory circuitry in human embryonic stem cells. Cell 122, 947-956.

Breitman, T. R., Collins, S. J., and Keene, B. R. (1981). Terminal differentiation of human promyelocytic leukemic cells in primary culture in response to retinoic acid. Blood 57, 1000-1004.

Breitman, T. R., Selonick, S. E., and Collins, S. J. (1980). Induction of differentiation of the human promyelocytic leukemia cell line (HL-60) by retinoic acid. Proc Natl Acad Sci USA 77, 2936-2940.

Burnett, A. K., Hills, R. K., Green, C., Jenkinson, S., Koo, K., Patel, Y., Guy, C., Gilkes, A., Milligan, D. W., Goldstone, A. H., et al. (2010). The impact on outcome of the addition of all-trans retinoic acid to intensive chemotherapy in younger patients with nonacute promyelocytic acute myeloid leukemia: overall results and results in genotypic subgroups defined by mutations in NPM1, FLT3, and CEBPA Blood 115, 948-956.

Chadwick, K., Wang, L., Li, L., Menendez, P., Murdoch, B., Rouleau, A., and Bhatia, M. (2003). Cytokines and BMP-4 promote hematopoietic differentiation of human embryonic stem cells. Blood 102, 906-915.

Dalton, S. O., Johansen, C., Poulsen, A. H., Norgaard, M., Sorensen, H. T., McLaughlin, J. K., Mortensen, P. B., and Friis, S. (2006). Cancer risk among users of neuroleptic medication: a population-based cohort study. Br J Cancer 95, 934-939.

Dalton, S. O., Mellemkjaer, L., Thomassen, L., Mortensen, P. B., and Johansen, C. (2005). Risk for cancer in a cohort of patients hospitalized for schizophrenia in Denmark, 1969-1993. Schizophr Res 75, 315-324.

Desbordes, S. C., Placantonakis, D. G., Ciro, A., Socci, N. D., Lee, G., Djaballah, H., and Studer, L. (2008). High-throughput screening assay for the identification of compounds regulating self-renewal and differentiation in human embryonic stem cells. Cell Stem Cell 2, 602-612.

Diallo, J. S., Le Boeuf, F., Lai, F., Cox, J., Vaha-Koskela, M., Abdelbary, H., MacTavish, H., Waite, K., Falls, T., Wang, J., et al. (2010). A high-throughput pharmacoviral approach identifies novel oncolytic virus sensitizers. Mol Ther 18, 1123-1129.

Dick, J. E. (2008). Stem cell concepts renew cancer research. Blood 112, 4793-4807.

Dick, J. E. (2009). Looking ahead in cancer stem cell research. Nat Biotechnol 27, 44-46.

Driver, J. A., Logroscino, G., Buring, J. E., Gaziano, J. M., and Kurth, T. (2007). A prospective cohort study of cancer incidence following the diagnosis of Parkinson's disease. Cancer Epidemiol Biomarkers Prey 16, 1260-1265.

Eppert, K., Takenaka, K., Lechman, E. R., Waldron, L., Nilsson, B., van Galen, P., Metzeler, K. H., Poeppl, A., Ling, V., Beyene, J., et al. (2011). Stem cell gene expression programs influence clinical outcome in human leukemia. Nature Medicine doi:10.1038/nm.2415.

Estey, E., and Dohner, H. (2006). Acute myeloid leukaemia. Lancet 368, 1894-1907.

Estey, E. H., Thall, P. F., Pierce, S., Cortes, J., Beran, M., Kantarjian, H., Keating, M. J., Andreeff, M., and Freireich, E. (1999). Randomized phase II study of fludarabine+cytosine arabinoside+idarubicin+/−all-trans retinoic acid+/−granulocyte colony-stimulating factor in poor prognosis newly diagnosed acute myeloid leukemia and myelodysplastic syndrome. Blood 93, 2478-2484.

Fibach, E., Hayashi, M., and Sachs, L. (1973). Control of normal differentiation of myeloid leukemic cells to macrophages and granulocytes. Proc Natl Acad Sci USA 70, 343-346.

Frese, K. K., and Tuveson, D. A. (2007). Maximizing mouse cancer models. Nat Rev Cancer 7, 645-658.

Friend, C., Scher, W., Holland, J. G., and Sato, T. (1971). Hemoglobin synthesis in murine virus-induced leukemic cells in vitro: stimulation of erythroid differentiation by dimethyl sulfoxide. Proc Natl Acad Sci USA 68, 378-382.

Grant, Steven. New agents for AML and MDS. *Best Practice & Research Clinical Haematology* 22 (2009) 501-507.

Guan, Y., Gerhard, B., and Hogge, D. E. (2003). Detection, isolation, and stimulation of quiescent primitive leukemic progenitor cells from patients with acute myeloid leukemia (AML). Blood 101, 3142-3149.

Gupta, P. B., Onder, T. T., Jiang, G., Tao, K., Kuperwasser, C., Weinberg, R. A., and Lander, E. S. (2009). Identification of selective inhibitors of cancer stem cells by high-throughput screening. Cell 138, 645-659.

Hotta, A., Cheung, A. Y., Farra, N., Vijayaragavan, K., Seguin, C. A., Draper, J. S., Pasceri, P., Maksakova, I. A., Mager, D. L., Rossant, J., et al. (2009). Isolation of human iPS cells using EOS lentiviral vectors to select for pluripotency. Nat Methods 6, 370-376.

Inglese, J., Shamu, C. E., and Guy, R. K. (2007). Reporting data from high-throughput screening of small-molecule libraries. Nat Chem Biol 3, 438-441.

Jemal, A., Siegel, R., Xu, J., and Ward, E. (2010). Cancer statistics, 2010. CA Cancer J Clin 60, 277-300.

Jordan, C. T. (2009). Cancer stem cells: controversial or just misunderstood? Cell Stem Cell 4, 203-205.

Koistinen P et al., Regulation of the acute myeloid leukemia cell line OCI/AML-2 by endothelial nitric oxide synthase under the control of a vascular endothelial growth factor signaling system. Leukemia. 2001 September; 15(9):1433-41.

Lapidot, T., Sirard, C., Vormoor, J., Murdoch, B., Hoang, T., Caceres-Cortes, J., Minden, M., Paterson, B., Caligiuri, M. A., and Dick, J. E. (1994). A cell initiating human acute myeloid leukaemia after transplantation into SCID mice. Nature 367, 645-648.

Lee, J. Y., Nakada, D., Yilmaz, O. H., Tothova, Z., Joseph, N. M., Lim, M. S., Gilliland, D. G., and Morrison, S. J. (2010). mTOR activation induces tumor suppressors that inhibit leukemogenesis and deplete hematopoietic stem cells after Pten deletion. Cell Stem Cell 7, 593-605.

Li, X., Lewis, M. T., Huang, J., Gutierrez, C., Osborne, C. K., Wu, M. F., Hilsenbeck, S. G., Pavlick, A., Zhang, X., Chamness, G. C., et al. (2008). Intrinsic resistance of tumorigenic breast cancer cells to chemotherapy. J Natl Cancer Inst 100, 672-679.

Little, K. Y., Elmer, L. W., Zhong, H., Scheys, J. O., and Zhang, L. (2002). Cocaine induction of dopamine transporter trafficking to the plasma membrane. Mol Pharmacol 61, 436-445.

Nasr, R., Guillemin, M. C., Ferhi, O., Soilihi, H., Peres, L., Berthier, C., Rousselot, P., Robledo-Sarmiento, M., Lallemand-Breitenbach, V., Gourmel, B., et al. (2008). Eradication of acute promyelocytic leukemia-initiating cells through PML-RARA degradation. Nat Med 14, 1333-1342.

Nichols, J., Zevnik, B., Anastassiadis, K., Niwa, H., Klewe-Nebenius, D., Chambers, I., Scholer, H., and Smith, A. (1998). Formation of pluripotent stem cells in the mammalian embryo depends on the POU transcription factor Oct4. Cell 95, 379-391.

Niu, C., Yan, H., Yu, T., Sun, H. P., Liu, J. X., Li, X. S., Wu, W., Zhang, F. Q., Chen, Y., Zhou, L., et al. (1999). Studies on treatment of acute promyelocytic leukemia with arsenic trioxide: remission induction, follow-up, and molecular monitoring in 11 newly diagnosed and 47 relapsed acute promyelocytic leukemia patients. Blood 94, 3315-3324.

Niwa, H., Miyazaki, J., and Smith, A. G. (2000). Quantitative expression of Oct-3/4 defines differentiation, dedifferentiation or self-renewal of ES cells. Nat Genet 24, 372-376.

William B. Parker "Enzymology of Purine and Pyrimidine Antimetabolites Used in the Treatment of Cancer" Chem Rev. 2009 July; 109(7): 2880-2893.

Raj, L., Ide, T., Gurkar, A. U., Foley, M., Schenone, M., Li, X., Tolliday, N. J., Golub, T. R., Carr, S. A., Shamji, A. F., et al. (2011). Selective killing of cancer cells by a small molecule targeting the stress response to ROS. Nature 475, 231-234.

Recher, C., Beyne-Rauzy, O., Demur, C., Chicanne, G., Dos Santos, C., Mas, V. M., Benzaquen, D., Laurent, G., Huguet, F., and Payrastre, B. (2005). Antileukemic activity of rapamycin in acute myeloid leukemia. Blood 105, 2527-2534.

Regenthal, R., Krueger, M., Koeppel, C., and Preiss, R. (1999). Drug levels: therapeutic and toxic serum/plasma concentrations of common drugs. J Clin Monit Comput 15, 529-544.

Reya, T., Morrison, S. J., Clarke, M. F., and Weissman, I. L. (2001). Stem cells, cancer, and cancer stem cells. Nature 414, 105-111.

Sachs, L. (1978a). Control of normal cell differentiation and the phenotypic reversion of malignancy in myeloid leukaemia. Nature 274, 535-539.

Sachs, L. (1978b). The differentiation of myeloid leukaemia cells: new possibilities for therapy. Br J Haematol 40, 509-517.

Sanz, M. A. (2006). Treatment of acute promyelocytic leukemia. Hematology Am Soc Hematol Educ Program, 147-155.

Sanz, M. A., Grimwade, D., Tallman, M. S., Lowenberg, B., Fenaux, P., Estey, E. H., Naoe, T., Lengfelder, E., Buchner, T., Dohner, H., et al. (2009). Management of acute promyelocytic leukemia: recommendations from an expert panel on behalf of the European LeukemiaNet. Blood 113, 1875-1891.

Seeman, P., and Lee, T. (1975). Antipsychotic drugs: direct correlation between clinical potency and presynaptic action on dopamine neurons. Science 188, 1217-1219.

Self, D. W., Barnhart, W. J., Lehman, D. A., and Nestler, E. J. (1996). Opposite modulation of cocaine—seeking behavior by D1- and D2-like dopamine receptor agonists. Science 271, 1586-1589.

Shoemaker, R. H. (2006). The NCI60 human tumour cell line anticancer drug screen. Nat Rev Cancer 6, 813-823.

Sibley, D. R., and Monsma, F. J., Jr. (1992). Molecular biology of dopamine receptors. Trends Pharmacol Sci 13, 61-69.

Smith, B. D., Levis, M., Beran, M., Giles, F., Kantarjian, H., Berg, K., Murphy, K. M., Dauses, T., Allebach, J., and Small, D. (2004). Single-agent CEP-701, a novel FLT3 inhibitor, shows biologic and clinical activity in patients with relapsed or refractory acute myeloid leukemia. Blood 103, 3669-3676.

Smith, T. J., Khatcheressian, J., Lyman, G. H., Ozer, H., Armitage, J. O., Balducci, L., Bennett, C. L., Cantor, S. B., Crawford, J., Cross, S. J., et al. (2006). 2006 update of recommendations for the use of white blood cell growth factors: an evidence-based clinical practice guideline. J Clin Oncol 24, 3187-3205.

Taussig, D. C., Miraki-Moud, F., Anjos-Afonso, F., Pearce, D. J., Allen, K., Ridler, C., Lillington, D., Oakervee, H., Cavenagh, J., Agrawal, S. G., et al. (2008). Anti-CD38 antibody-mediated clearance of human repopulating cells masks the heterogeneity of leukemia-initiating cells. Blood 112, 568-575.

Tefferi et al. Cancer, September $1^{st}$, pp. 3842-3847 (2009)

Vannucchi et al. Advances in Understanding and Management of Myeloproliferative Neoplasms CA Cancer J. Clin. 2009; 59:171-191

Visvader, J. E., and Lindeman, G. J. (2008). Cancer stem cells in solid tumours: accumulating evidence and unresolved questions. Nat Rev Cancer 8, 755-768.

Wang, Z. Y., and Chen, Z. (2008). Acute promyelocytic leukemia: from highly fatal to highly curable. Blood 111, 2505-2515.

Werbowetski-Ogilvie, T. E., Bosse, M., Stewart, M., Schnerch, A., Ramos-Mejia, V., Rouleau, A., Wynder, T., Smith, M. J., Dingwall, S., Carter, T., et al. (2009). Characterization of human embryonic stem cells with features of neoplastic progression. Nat Biotechnol 27, 91-97.

Xu, R. H., Chen, X., Li, D. S., Li, R., Addicks, G. C., Glennon, C., Zwaka, T. P., and Thomson, J. A. (2002). BMP4 initiates human embryonic stem cell differentiation to trophoblast. Nat Biotechnol 20, 1261-1264.

Yilmaz, O. H., Valdez, R., Theisen, B. K., Guo, W., Ferguson, D. O., Wu, H., and Morrison, S. J. (2006). Pten dependence distinguishes haematopoietic stem cells from leukaemia-initiating cells. Nature 441, 475-482.

Ying, Q. L., Nichols, J., Chambers, I., and Smith, A. (2003). BMP induction of Id proteins suppresses differentiation and sustains embryonic stem cell self-renewal in collaboration with STAT3. Cell 115, 281-292.

Yoshida, H., Kitamura, K., Tanaka, K., Omura, S., Miyazaki, T., Hachiya, T., Ohno, R., and Naoe, T. (1996). Accelerated degradation of PML-retinoic acid receptor alpha (PML-RARA) oncoprotein by all-trans-retinoic acid in acute promyelocytic leukemia: possible role of the proteasome pathway. Cancer Res 56, 2945-2948.

Zhelev, Z., Ohba, H., Bakalova, R., Hadjimitova, V., Ishikawa, M., Shinohara, Y., and Baba, Y. (2004). Phenothiazines suppress proliferation and induce apoptosis in cultured leukemic cells without any influence on the viability of normal lymphocytes. Phenothiazines and leukemia. Cancer Chemother Pharmacol 53, 267-275.

Zheng, R., Friedman, A. D., and Small, D. (2002). Targeted inhibition of FLT3 overcomes the block to myeloid differentiation in 32Dcl3 cells caused by expression of FLT3/ITD mutations. Blood 100, 4154-4161.

Zhu, J., Koken, M. H., Quignon, F., Chelbi-Alix, M. K., Degos, L., Wang, Z. Y., Chen, Z., and de The, H. (1997). Arsenic-induced PML targeting onto nuclear bodies: implications for the treatment of acutepromyelocytic leukemia. Proc Natl Acad Sci USA 94, 3978-3983.

The invention claimed is:

1. A method of treating acute myeloid leukemia in a subject in need thereof comprising administering to the subject thioridazine and cytarabine.

2. The method of claim 1, wherein thioridazine and cytarabine are administered to the subject at the same time.

3. The method of claim 1, wherein thioridazine and cytarabine are administered to the subject at different times.

4. The method of claim 1, wherein cytarabine is administered to the subject such that the plasma concentration of cytarabine in the subject is between 1 nM and 100 nM.

5. The method of claim 4, wherein cytarabine is administered to the subject such that the plasma concentration of cytarabine in the subject is less than 5 nM.

6. The method of claim 1, wherein thoridazine is administered to the subject such that the plasma concentration of thioridazine in the subject is between 5 μM and 15 μM.

7. The method of claim 1, wherein thioridazine is administered to the subject such that the plasma concentration of thioridazine in the subject is about 10 μM.

8. The method of claim 1, wherein cytarabine is administered to the subject such that the plasma concentration of cytarabine in the subject is between 1 nM and 100 nM and thioridazine is administered to the subject such that the plasma concentration of thioridazine in the subject is between 5 μM and 15 μM.

9. The method of claim 8, wherein thioridazine is administered to the subject such that the plasma concentration of thioridazine in the subject is about 10 μM.

10. A method for reducing the proliferation of one or more leukemic cells comprising contacting the cells with thioridazine and cytarabine.

11. The method of claim 10, wherein the leukemic cell is an acute myeloid leukemia (AML) cell.

12. The method of claim 10, wherein the leukemic cell is a leukemic cancer stem cell.

13. The method of claim 10, wherein the cell is in vivo or in vitro.

14. The method of claim 10, wherein the cell is contacted with cytarabine at a concentration between 1 nM and 100 nM.

15. The method of claim 14, wherein the cell is contacted with cytarabine at a concentration of less than 5 nM.

16. The method of claim 10, wherein the cell is contacted with thioridazine at a concentration between 5 μM and 15 μM.

17. The method of claim 10, wherein the cell is contacted with thioridazine at a concentration of about 10 μM.

18. The method of claim 10, wherein the cell is contacted with cytarabine at a concentration between 1 nM and 100 nM and the cell is contacted with thioridazine at a concentration between 5 μM and 15 μM.

19. The method of claim 18, wherein the cell is contacted with thioridazine at a concentration of about 10 μM.

20. A composition comprising thioridazine, cytarabine and a pharmaceutically acceptable carrier.

* * * * *